United States Patent
An et al.

(10) Patent No.: US 10,478,629 B2
(45) Date of Patent: *Nov. 19, 2019

(54) LEADLESS CARDIAC PACEMAKER FOR GENERATING CARDIAC PRESSURE VOLUME LOOP

(71) Applicant: CARDIAC PACEMAKERS, INC., St. Paul, MN (US)

(72) Inventors: Qi An, Blaine, MN (US); Pramodsingh Hirasingh Thakur, Woodbury, MN (US); Yinghong Yu, Shoreview, MN (US); Jeffrey E. Stahmann, Ramsey, MN (US); Michael J. Kane, St. Paul, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 7 days.

This patent is subject to a terminal disclaimer.

(21) Appl. No.: 15/630,677

(22) Filed: Jun. 22, 2017

(65) Prior Publication Data

US 2018/0021584 A1    Jan. 25, 2018

Related U.S. Application Data

(60) Provisional application No. 62/364,612, filed on Jul. 20, 2016.

(51) Int. Cl.
*A61N 1/375* (2006.01)
*A61N 1/372* (2006.01)
(Continued)

(52) U.S. Cl.
CPC ............. *A61N 1/3756* (2013.01); *A61B 5/00* (2013.01); *A61B 5/0031* (2013.01); *A61B 5/029* (2013.01);
(Continued)

(58) Field of Classification Search
CPC .... A61N 1/3756; A61N 1/025; A61N 1/0565; A61N 1/0573; A61N 1/36521
See application file for complete search history.

(56) References Cited

U.S. PATENT DOCUMENTS 6,141,588 A * 10/2000 Cox ..................... A61N 1/3622
128/903
7,212,861 B1   5/2007 Park et al.
(Continued)

FOREIGN PATENT DOCUMENTS

| EP | 2280759 B1 | 6/2015 |
| WO | 2007033094 A2 | 3/2007 |
| WO | 20090131768 A1 | 10/2009 |

OTHER PUBLICATIONS

"Complete PV Loop Analysis," Millar, pp. 1-4, 2014.
Roest et al., "Prediction of Long-term Outcome of Cardiac Resynchronization Therapy by Acute Pressure-volume Loop Measurements," European Journal of Heart Failure, 15: 299-307, 2013.

*Primary Examiner* — Joseph M Dietrich
(74) *Attorney, Agent, or Firm* — Seager, Tufte & Wickhem LLP

(57) ABSTRACT

A leadless cardiac pacemaker (LCP) configured to sense cardiac activity and to pace a patient's heart. The LCP may include a housing, a first electrode secured relative to the housing, a second electrode secured relative to the housing, and a pressure sensor secured relative to the housing and coupled to the environment outside of the housing. The LCP may further include circuitry in the housing in communication with the first electrode, the second electrode, and the pressure sensor. The circuitry may be configured to determine and store a plurality of impedance-pressure data pairs, from which a representation of a pressure-volume loop may be determined.

20 Claims, 14 Drawing Sheets

(51) Int. Cl.
*A61N 1/365* (2006.01)
*A61N 1/05* (2006.01)
*A61N 1/02* (2006.01)
*A61N 1/37* (2006.01)
*A61B 5/00* (2006.01)
*A61B 5/0215* (2006.01)
*A61B 5/029* (2006.01)
*A61B 5/053* (2006.01)
*A61B 7/00* (2006.01)
*A61N 1/378* (2006.01)

(52) U.S. Cl.
CPC .......... *A61B 5/0215* (2013.01); *A61B 5/0538* (2013.01); *A61B 5/686* (2013.01); *A61B 7/00* (2013.01); *A61N 1/025* (2013.01); *A61N 1/0565* (2013.01); *A61N 1/0573* (2013.01); *A61N 1/36521* (2013.01); *A61N 1/36564* (2013.01); *A61N 1/36585* (2013.01); *A61N 1/3704* (2013.01); *A61N 1/3727* (2013.01); *A61N 1/37217* (2013.01); *A61N 1/37223* (2013.01); *A61N 1/37247* (2013.01); *A61N 1/37264* (2013.01); *A61N 1/378* (2013.01); *A61N 1/3758* (2013.01); *A61N 1/37205* (2013.01); *A61N 1/37211* (2013.01); *A61N 1/37512* (2017.08)

(56) References Cited

U.S. PATENT DOCUMENTS

| | | | |
|---|---|---|---|
| 7,286,875 | B1 | 10/2007 | Park et al. |
| 7,580,746 | B2 | 8/2009 | Gilkerson et al. |
| 7,596,412 | B1 | 9/2009 | Kroll |
| 7,702,392 | B2 | 4/2010 | Echt et al. |
| 8,306,621 | B2 | 11/2012 | Kim et al. |
| 8,478,400 | B2 | 7/2013 | Hettrick et al. |
| 8,521,265 | B2 | 8/2013 | Vollkron et al. |
| 8,831,721 | B2 | 9/2014 | Hettrick et al. |
| 2007/0060961 | A1 | 3/2007 | Echt et al. |
| 2008/0195167 | A1 | 8/2008 | Ryan |
| 2010/0113945 | A1 | 5/2010 | Ryan |
| 2014/0277240 | A1 | 9/2014 | Maskara et al. |

* cited by examiner

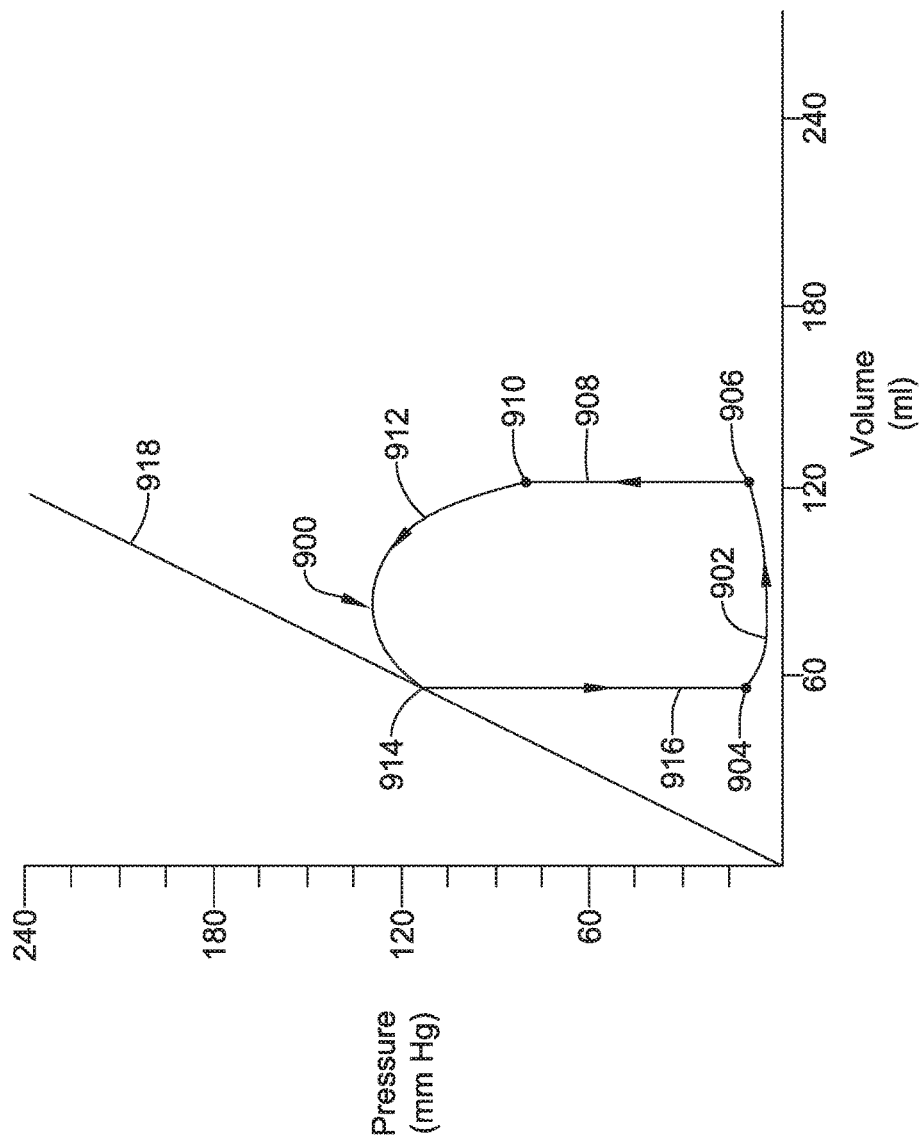

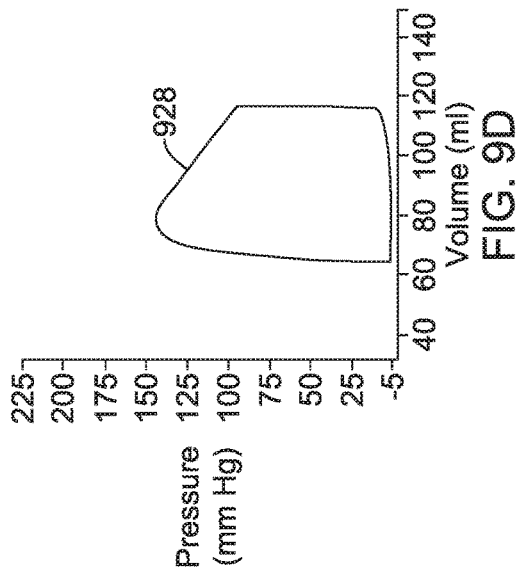
FIG. 9C
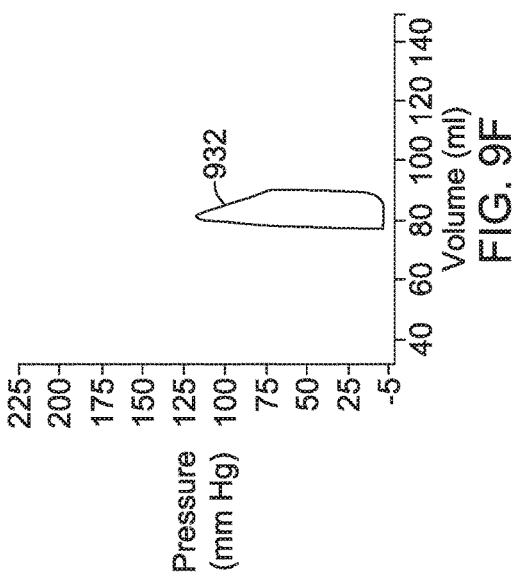
FIG. 9D
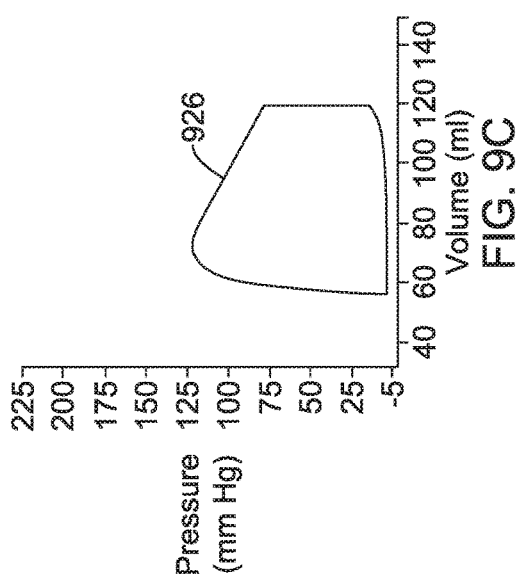
FIG. 9E
FIG. 9F

LEADLESS CARDIAC PACEMAKER FOR GENERATING CARDIAC PRESSURE VOLUME LOOP

CROSS REFERENCE TO RELATED APPLICATIONS

This application claims the benefit of U.S. Provisional Patent Application Ser. No. 62/364,612 filed on Jul. 20, 2016, the disclosure of which is incorporated herein by reference.

TECHNICAL FIELD

The present disclosure generally relates to implantable medical devices and more particularly to implantable leadless cardiac pacemakers

BACKGROUND

Pacing instruments can be used to treat patients suffering from various heart conditions that may result in a reduced ability of the heart to deliver sufficient amounts of blood to a patient's body. These heart conditions may lead to rapid, irregular, and/or inefficient heart contractions. To help alleviate some of these conditions, various devices (e.g., pacemakers, defibrillators, etc.) are often implanted in a patient's body. Such devices may monitor and provide therapy such as electrical stimulation therapy to the heart to help the heart operate in a more normal, efficient and/or safe manner. In some cases, a patient may have multiple implanted devices that cooperate to monitor and/or provide therapy to the patient's heart.

SUMMARY

The present disclosure generally relates to implantable medical devices and more particularly to implantable leadless cardiac pacemakers.

In a first example, a leadless cardiac pacemaker (LCP) configured to sense cardiac activity and to pace a patient's heart may comprise a housing, a first electrode secured relative to the housing and exposed to the environment outside of the housing, a second electrode secured relative to the housing and exposed to the environment outside of the housing, the second electrode is spaced from the first electrode, a pressure sensor secured relative to the housing and is coupled to the environment outside of the housing, and circuitry in the housing in communication with the first electrode, the second electrode, and the pressure sensor, the circuitry configured to determine, at a first time during a cardiac cycle, a first impedance between the first electrode and the second electrode and also a corresponding first pressure via the pressure sensor, resulting in a first impedance-pressure data pair.

Alternatively or additionally to any of the examples above, in another example, the circuitry may be configured to wirelessly transmit the first impedance-pressure data pair to a remote device.

Alternatively or additionally to any of the examples above, in another example, the circuitry may be configured to determine, at a second time during the cardiac cycle, a second impedance between the first electrode and the second electrode and also a second pressure via the pressure sensor, resulting in a second impedance-pressure data pair.

Alternatively or additionally to any of the examples above, in another example, the first time may correspond to an S1 heart sound and the second time may correspond to an S2 heart sound.

Alternatively or additionally to any of the examples above, in another example, the circuitry may be further configured to determine, at a plurality of times between the first time and the second time, a plurality of corresponding impedances between the first electrode and the second electrode and also corresponding pressures via the pressure sensor, resulting in a plurality of additional impedance-pressure data pairs.

Alternatively or additionally to any of the examples above, in another example, the circuitry may be further configured to wirelessly transmit the first impedance-pressure data pair, the second impedance-pressure data pair, and the plurality of additional impedance-pressure data pairs to a remote device.

Alternatively or additionally to any of the examples above, in another example, the remote device may be configured to generate and display a pressure-volume loop that may be based at least in part on the first impedance-pressure data pair, the second impedance-pressure data pair, and the plurality of additional impedance-pressure data pairs.

Alternatively or additionally to any of the examples above, in another example, the remote device may be configured to store and display a plurality of pressure-volume loops generated over a period of time.

Alternatively or additionally to any of the examples above, in another example, the circuitry may be further configured to record contextual data regarding a patient's metabolic demands.

Alternatively or additionally to any of the examples above, in another example, the circuitry may be configured to determine, at a first time during each of a plurality of cardiac cycles, the first impedance between the first electrode and the second electrode and also the corresponding first pressure via the pressure sensor, resulting in the first impedance-pressure data pair for each of the plurality of cardiac cycles.

Alternatively or additionally to any of the examples above, in another example, the circuitry may be further configured to average the first impedance and the first pressure over the plurality of cardiac cycles, resulting in an averaged first impedance-pressure data pair.

Alternatively or additionally to any of the examples above, in another example, the circuitry may comprise energy delivery circuitry operatively coupled to the first electrode and the second electrode for causing a current to flow between the first electrode and the second electrode and detection circuitry operatively coupled to the first electrode and the second electrode for detecting an electrical signal received between the first electrode and the second electrode.

Alternatively or additionally to any of the examples above, in another example, the energy delivery circuitry may provide a current between the first electrode and the second electrode and the detection circuitry may measure a resulting voltage between the first electrode and the second electrode to determine the impedance between the first electrode and the second electrode.

Alternatively or additionally to any of the examples above, in another example, the energy delivery circuitry may provide a voltage between the first electrode and the second electrode and the detection circuitry may measure a resulting current between the first electrode and the second electrode to determine the impedance between the first electrode and the second electrode.

Alternatively or additionally to any of the examples above, in another example, the energy delivery circuitry may be further configured to deliver pacing pulses via the first electrode and the second electrode.

In another example, a leadless cardiac pacemaker (LCP) configured to sense cardiac activity and to pace a patient's heart may comprise a housing, a first electrode secured relative to the housing and exposed to the environment outside of the housing, a second electrode secured relative to the housing and exposed to the environment outside of the housing, the second electrode may be spaced from the first electrode, a pressure sensor secured relative to the housing and may be coupled to the environment outside of the housing and circuitry in the housing in communication with the first electrode, the second electrode, and the pressure sensor, the circuitry configured to determine, at a first time during a cardiac cycle, a first impedance between the first electrode and the second electrode and also a corresponding first pressure via the pressure sensor, resulting in a first impedance-pressure data pair.

Alternatively or additionally to any of the examples above, in another example, the circuitry may be configured to wirelessly transmit the first impedance-pressure data pair to a remote device.

Alternatively or additionally to any of the examples above, in another example, the circuitry may be configured to determine, at a second time during the cardiac cycle, a second impedance between the first electrode and the second electrode and also a second pressure via the pressure sensor, resulting in a second impedance-pressure data pair.

Alternatively or additionally to any of the examples above, in another example, the first time may correspond to an S1 heart sound and the second time may correspond to an S2 heart sound.

Alternatively or additionally to any of the examples above, in another example, the circuitry may be further configured to determine, at a plurality of times between the first time and the second time, a plurality of corresponding impedances between the first electrode and the second electrode and also corresponding pressures via the pressure sensor, resulting in a plurality of additional impedance-pressure data pairs.

Alternatively or additionally to any of the examples above, in another example, the circuitry may be further configured to wirelessly transmit the first impedance-pressure data pair, the second impedance-pressure data pair, and the plurality of additional impedance-pressure data pairs to a remote device.

Alternatively or additionally to any of the examples above, in another example, the remote device may be configured to generate and display a pressure-volume loop that may be based at least in part on the first impedance-pressure data pair, the second impedance-pressure data pair, and the plurality of additional impedance-pressure data pairs.

Alternatively or additionally to any of the examples above, in another example, the remote device may be configured to store and display a plurality of pressure-volume loops generated over a period of time.

Alternatively or additionally to any of the examples above, in another example, the circuitry may be further configured to record contextual data regarding a patient's metabolic demands.

Alternatively or additionally to any of the examples above, in another example, wherein the circuitry may be configured to determine, at a first time during each of a plurality of cardiac cycles, the first impedance between the first electrode and the second electrode and also the corresponding first pressure via the pressure sensor, resulting in the first impedance-pressure data pair for each of the plurality of cardiac cycles.

Alternatively or additionally to any of the examples above, in another example, the circuitry may be further configured to average the first impedance and the first pressure over the plurality of cardiac cycles, resulting in an averaged first impedance-pressure data pair.

Alternatively or additionally to any of the examples above, in another example, the circuitry may comprise energy delivery circuitry operatively coupled to the first electrode and the second electrode for causing a current to flow between the first electrode and the second electrode and detection circuitry operatively coupled to the first electrode and the second electrode for detecting an electrical signal received between the first electrode and the second electrode.

Alternatively or additionally to any of the examples above, in another example, the energy delivery circuitry may provide a current between the first electrode and the second electrode and the detection circuitry may measure a resulting voltage between the first electrode and the second electrode to determine the impedance between the first electrode and the second electrode.

Alternatively or additionally to any of the examples above, in another example, the energy delivery circuitry may provide a voltage between the first electrode and the second electrode and the detection circuitry may measure a resulting current between the first electrode and the second electrode to determine the impedance between the first electrode and the second electrode.

Alternatively or additionally to any of the examples above, in another example, the energy delivery circuitry may be further configured to deliver pacing pulses via the first electrode and the second electrode.

Alternatively or additionally to any of the examples above, in another example, the detection circuitry may be further configured to detect cardiac signals received between the first electrode and the second electrode.

In another example, a leadless cardiac pacemaker (LCP) configured to sense cardiac activity and to pace a patient's heart may comprise a housing, a first electrode secured relative to the housing and exposed to the environment outside of the housing, a second electrode secured relative to the housing and exposed to the environment outside of the housing, the second electrode may be spaced from the first electrode, a pressure sensor secured relative to the housing and may be coupled to the environment outside of the housing, and circuitry in the housing in communication with the first electrode, the second electrode, and the pressure sensor, the circuitry configured to determine, at each of a plurality of times during each of a plurality of cardiac cycles, an impedance between the first electrode and the second electrode and also a corresponding pressure via the pressure sensor, resulting in a plurality of impedance-pressure data pairs for each of the plurality of cardiac cycles.

Alternatively or additionally to any of the examples above, in another example, the circuitry may be further configured to wirelessly transmit at least some of the plurality of impedance-pressure data pairs for each of the plurality of cardiac cycles to a remote device.

Alternatively or additionally to any of the examples above, in another example, the remote device may be configured to generate and display a pressure-volume loop based on the plurality of impedance-pressure data pairs for at least one of the plurality of cardiac cycles.

In another example, a system may comprise a leadless cardiac pacemaker (LCP) configured to sense and pace a patient's heart and an external support device comprising a processor and a display. The LCP may comprise a housing, a first electrode positioned proximate a distal end of the housing, a second electrode positioned proximate a proximal end of the housing, wherein a current flowing between the first electrode and the second electrode may be used to calculate impedance, a pressure sensor, and circuitry in communication with the first electrode, the second electrode, and the pressure sensor. The circuitry of the LCP may be configured to sample impedance between the first electrode and the second electrode and pressure at a plurality of times within each of a plurality of cardiac cycles, and to generate a plurality of impedance-pressure data pairs, the circuitry of the LCP further configured to transit the plurality of impedance-pressure data pairs to the external support device via conducted communication. The external support device may be configured to generate and display a pressure-volume loop using at least some of the plurality of impedance-pressure data pairs.

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which:

FIGS. 9A-9F are various illustrative pressure-volume loops for a ventricle of a human heart;

Figure 1:
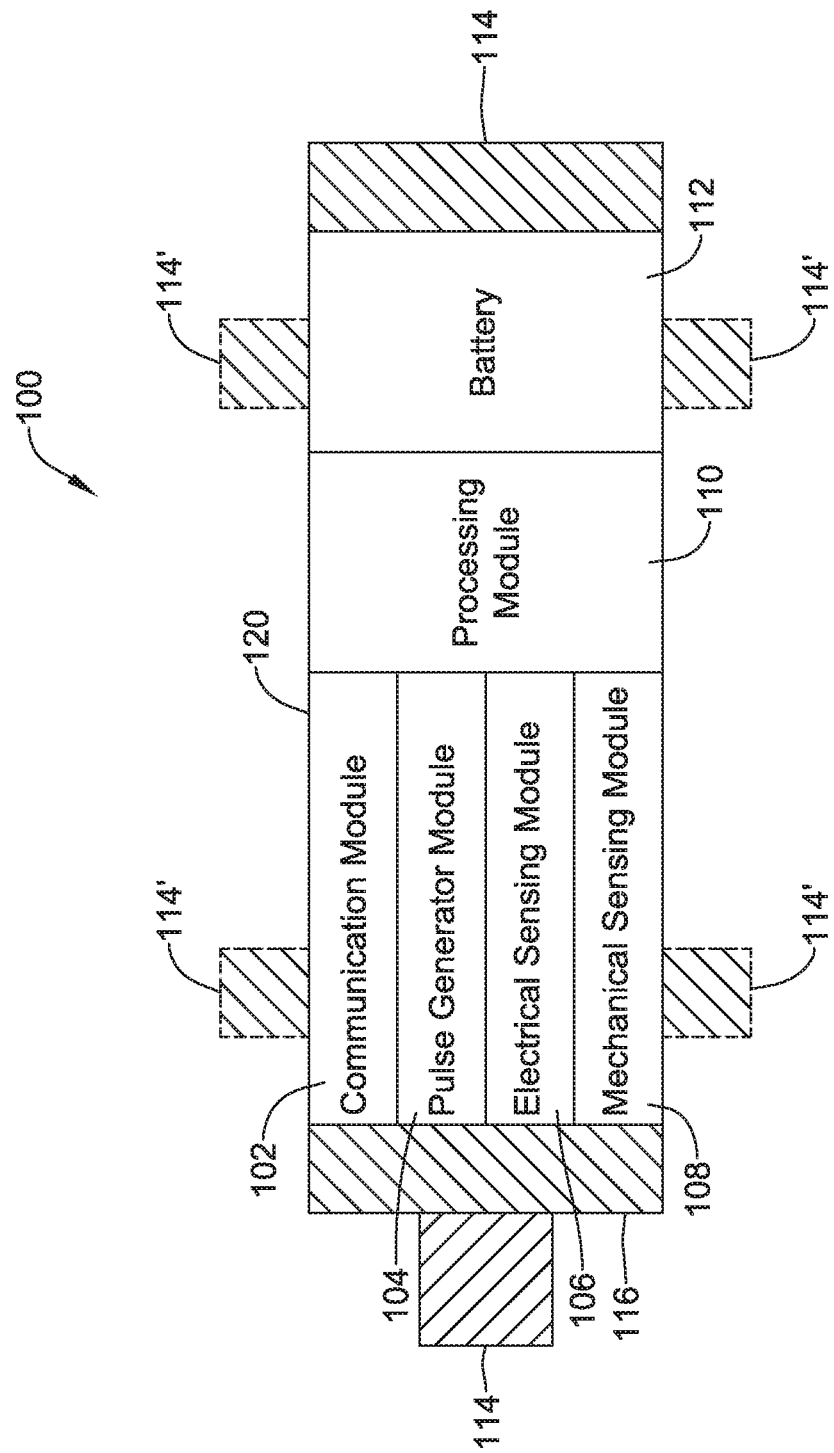
FIG. 1 is a schematic block diagram of an illustrative leadless cardiac pacemaker (LCP) according to one example of the present disclosure.

While the disclosure is amenable to various modifications and alternative forms, specifics thereof have been shown by way of example in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure.

A normal, healthy heart induces contraction by conducting intrinsically generated electrical signals throughout the heart. These intrinsic signals cause the muscle cells or tissue of the heart to contract. This contraction forces blood out of and into the heart, providing circulation of the blood throughout the rest of the body. However, many patients suffer from cardiac conditions that affect this contractility of their hearts. For example, some hearts may develop diseased tissues that no longer generate or conduct intrinsic electrical signals. In some examples, diseased cardiac tissues conduct electrical signals at differing rates, thereby causing an unsynchronized and inefficient contraction of the heart. In other examples, a heart may initiate intrinsic signals at such a low rate that the heart rate becomes dangerously low. In still other examples, a heart may generate electrical signals at an unusually high rate. In some cases such an abnormality can develop into a fibrillation state, where the contraction of the patient's heart chambers are almost completely desynchronized and the heart pumps very little to no blood. Implantable medical devices, which may be configured to determine occurrences of such cardiac abnormalities or arrhythmias and deliver one or more types of electrical stimulation therapy to patient's hearts, may help to terminate or alleviate these and other cardiac conditions.

FIG. 1 depicts an illustrative leadless cardiac pacemaker (LCP) that may be implanted into a patient and may operate to prevent, control, or terminate cardiac arrhythmias in patients by, for example, appropriately employing one or more therapies (e.g. anti-tachycardia pacing (ATP) therapy, cardiac resynchronization therapy (CRT), bradycardia therapy, defibrillation pulses, or the like). As can be seen in FIG. 1, the LCP 100 may be a compact device with all components housed within the LCP 100 or directly on the housing 120. In the example shown in FIG. 1, the LCP 100 may include a communication module 102, a pulse generator module 104, an electrical sensing module 106, a mechanical sensing module 108, a processing module 110, a battery 112, and electrodes 114. The LCP 100 may include more or less modules, depending on the application.

The communication module 102 may be configured to communicate with devices such as sensors, other medical devices, and/or the like, that are located externally to the LCP 100. Such devices may be located either external or internal to the patient's body. Irrespective of the location, remote devices (i.e. external to the LCP 100 but not necessarily external to the patient's body) can communicate with the LCP 100 via the communication module 102 to accomplish one or more desired functions. For example, the LCP 100 may communicate information, such as sensed electrical signals, data, instructions, messages, etc., to an external medical device through the communication module 102. The external medical device may use the communicated signals, data, instructions and/or messages to perform various functions, such as determining occurrences of arrhythmias, delivering electrical stimulation therapy, storing received data, analyzing received data, and/or performing any other suitable function. The LCP 100 may additionally receive information such as signals, data, instructions and/or messages from the external medical device through the communication module 102, and the LCP 100 may use the received signals, data, instructions and/or messages to perform various functions, such as determining occurrences of arrhythmias, delivering electrical stimulation therapy, storing received data, analyzing received data, and/or performing any other suitable function. The communication module 102 may be configured to use one or more methods for communicating with remote devices. For example, the communication module 102 may communicate via radiofrequency (RF) signals, inductive coupling, optical signals, acoustic signals, conducted communication signals, and/or any other signals suitable for communication.

In the example shown in FIG. 1, the pulse generator module 104 may be electrically connected to the electrodes 114. In some examples, LCP 100 may include one or more additional electrodes 114'. In such examples, the pulse generator 104 may also be electrically connected to the additional electrodes 114'. The pulse generator module 104 may be configured to generate electrical stimulation signals. For example, the pulse generator module 104 may generate electrical stimulation signals by using energy stored in a battery 112 within the LCP 100 and deliver the generated electrical stimulation signals via the electrodes 114 and/or 114'. Alternatively, or additionally, the pulse generator 104 may include one or more capacitors, and the pulse generator 104 may charge the one or more capacitors by drawing energy from the battery 112. The pulse generator 104 may then use the energy of the one or more capacitors to deliver the generated electrical stimulation signals via the electrodes 114 and/or 114'. In at least some examples, the pulse generator 104 of the LCP 100 may include switching circuitry to selectively connect one or more of the electrodes 114 and/or 114' to the pulse generator 104 in order to select which of the electrodes 114/114' (and/or other electrodes) the pulse generator 104 delivers the electrical stimulation therapy. The pulse generator module 104 may generate electrical stimulation signals with particular features or in particular sequences in order to provide one or multiple of a number of different stimulation therapies. For example, the pulse generator module 104 may be configured to generate electrical stimulation signals to provide electrical stimulation therapy to combat bradycardia, tachycardia, cardiac dyssynchrony, bradycardia arrhythmias, tachycardia arrhythmias, fibrillation arrhythmias, cardiac synchronization arrhythmias and/or to produce any other suitable electrical stimulation therapy. Some more common electrical stimulation therapies include bradycardia therapy, anti-tachycardia pacing (ATP) therapy, cardiac resynchronization therapy (CRT), and cardioversion/defibrillation therapy.

In some examples, the LCP 100 may not include a pulse generator 104 or may turn off the pulse generator 104. When so provided, the LCP 100 may be a diagnostic only device. In such examples, the LCP 100 may not deliver electrical stimulation therapy to a patient. Rather, the LCP 100 may collect data about cardiac electrical activity and/or physiological parameters of the patient and communicate such data and/or determinations to one or more other medical devices via the communication module 102.

In some examples, the LCP 100 may include an electrical sensing module 106, and in some cases, a mechanical sensing module 108. The electrical sensing module 106 may be configured to sense the cardiac electrical activity of the heart. For example, the electrical sensing module 106 may be connected to the electrodes 114/114', and the electrical sensing module 106 may be configured to receive cardiac electrical signals conducted through the electrodes 114/114'. The cardiac electrical signals may represent local information from the chamber in which the LCP 100 is implanted. For instance, if the LCP 100 is implanted within a ventricle of the heart, cardiac electrical signals sensed by the LCP 100 through the electrodes 114/114' may represent ventricular cardiac electrical signals. The mechanical sensing module 108 may include one or more sensors, such as an accelerometer, a blood pressure sensor, a heart sound sensor, a blood-oxygen sensor, a temperature sensor, a flow sensor and/or any other suitable sensors that are configured to measure one or more mechanical and/or chemical parameters of the patient.

Both the electrical sensing module 106 and the mechanical sensing module 108 may be connected to a processing module 110, which may provide signals representative of the sensed mechanical parameters. Although described with respect to FIG. 1 as separate sensing modules, in some cases, the electrical sensing module 106 and the mechanical sensing module 108 may be combined into a single sensing module, as desired.

The electrodes 114/114' can be secured relative to the housing 120 but exposed to the tissue and/or blood surrounding the LCP 100. In some cases, the electrodes 114 may be generally disposed on either end of the LCP 100 and may be in electrical communication with one or more of the modules 102, 104, 106, 108, and 110. The electrodes 114/114' may be supported by the housing 120, although in some examples, the electrodes 114/114' may be connected to the housing 120 through short connecting wires such that the electrodes 114/114' are not directly secured relative to the housing 120. In examples where the LCP 100 includes one or more electrodes 114', the electrodes 114' may in some cases be disposed on the sides of the LCP 100, which may increase the number of electrodes by which the LCP 100 may sense cardiac electrical activity, deliver electrical stimulation and/or communicate with an external medical device. The electrodes 114/114' can be made up of one or more biocompatible conductive materials such as various metals or alloys that are known to be safe for implantation within a human body. In some instances, the electrodes 114/114' connected to LCP 100 may have an insulative portion that electrically isolates the electrodes 114/114' from adjacent electrodes, the housing 120, and/or other parts of the LCP 100.

The processing module 110 can be configured to control the operation of the LCP 100. For example, the processing module 110 may be configured to receive electrical signals from the electrical sensing module 106 and/or the mechanical sensing module 108. Based on the received signals, the processing module 110 may determine, for example, occurrences and, in some cases, types of arrhythmias. Based on any determined arrhythmias, the processing module 110 may control the pulse generator module 104 to generate electrical stimulation in accordance with one or more therapies to treat the determined arrhythmia(s). The processing module 110 may further receive information from the communication module 102. In some examples, the processing module 110 may use such received information to help determine whether an arrhythmia is occurring, determine a type of arrhythmia, and/or to take particular action in response to the information. The processing module 110 may additionally control the communication module 102 to send/receive information to/from other devices.

In some examples, the processing module 110 may include a pre-programmed chip, such as a very-large-scale integration (VLSI) chip and/or an application specific integrated circuit (ASIC). In such embodiments, the chip may be pre-programmed with control logic in order to control the operation of the LCP 100. By using a pre-programmed chip, the processing module 110 may use less power than other programmable circuits (e.g. general purpose programmable microprocessors) while still being able to maintain basic functionality, thereby potentially increasing the battery life of the LCP 100. In other examples, the processing module 110 may include a programmable microprocessor. Such a programmable microprocessor may allow a user to modify the control logic of the LCP 100 even after implantation, thereby allowing for greater flexibility of the LCP 100 than when using a pre-programmed ASIC. In some examples, the processing module 110 may further include a memory, and the processing module 110 may store information on and read information from the memory. In other examples, the LCP 100 may include a separate memory (not shown) that is in communication with the processing module 110, such that the processing module 110 may read and write information to and from the separate memory.

The battery 112 may provide power to the LCP 100 for its operations. In some examples, the battery 112 may be a non-rechargeable lithium-based battery. In other examples, a non-rechargeable battery may be made from other suitable materials, as desired. Because the LCP 100 is an implantable device, access to the LCP 100 may be limited after implantation. Accordingly, it is desirable to have sufficient battery capacity to deliver therapy over a period of treatment such as days, weeks, months, years or even decades. In some instances, the battery 112 may a rechargeable battery, which may help increase the useable lifespan of the LCP 100. In still other examples, the battery 112 may be some other type of power source, as desired.

To implant the LCP 100 inside a patient's body, an operator (e.g., a physician, clinician, etc.), may fix the LCP 100 to the cardiac tissue of the patient's heart. To facilitate fixation, the LCP 100 may include one or more anchors 116. The anchor 116 may include any one of a number of fixation or anchoring mechanisms. For example, the anchor 116 may include one or more pins, staples, threads, screws, helix, tines, and/or the like. In some examples, although not shown, the anchor 116 may include threads on its external surface that may run along at least a partial length of the anchor 116. The threads may provide friction between the cardiac tissue and the anchor to help fix the anchor 116 within the cardiac tissue. In other examples, the anchor 116 may include other structures such as barbs, spikes, or the like to facilitate engagement with the surrounding cardiac tissue.

Figure 2:
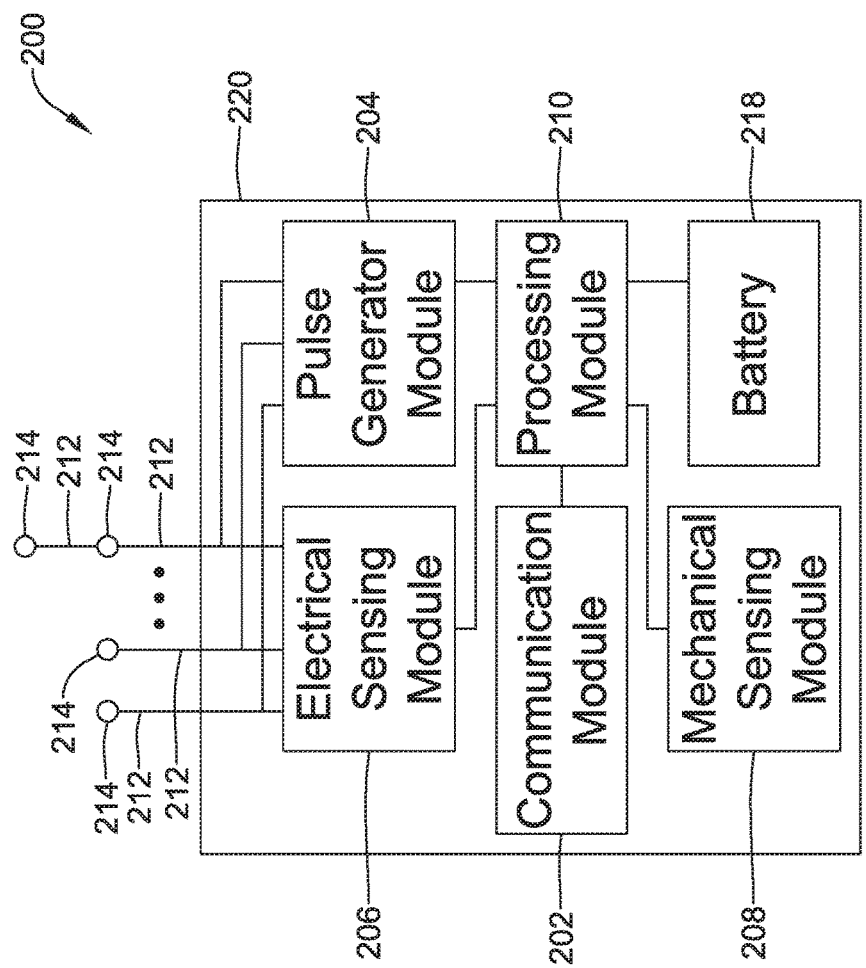
FIG. 2 is a schematic block diagram of another medical device (MD), which may be used in conjunction with an LCP 100 (FIG. 1) in order to detect and/or treat cardiac arrhythmias and other heart conditions.

FIG. 2 depicts an example of another medical device (MD) 200, which may be used in conjunction with an LCP 100 (FIG. 1) in order to detect and/or treat cardiac arrhythmias and other heart conditions. In the example shown, the MD 200 may include a communication module 202, a pulse generator module 204, an electrical sensing module 206, a mechanical sensing module 208, a processing module 210, and a battery 218. Each of these modules may be similar to the modules 102, 104, 106, 108, and 110 of the LCP 100. Additionally, the battery 218 may be similar to the battery 112 of the LCP 100. In some examples, the MD 200 may have a larger volume within the housing 220 than LCP 100. In such examples, the MD 200 may include a larger battery and/or a larger processing module 210 capable of handling more complex operations than the processing module 110 of the LCP 100.

While it is contemplated that the MD 200 may be another leadless device such as shown in FIG. 1, in some instances the MD 200 may include leads such as leads 212. The leads 212 may include electrical wires that conduct electrical signals between the electrodes 214 and one or more modules located within the housing 220. In some cases, the leads 212 may be connected to and extend away from the housing 220 of the MD 200. In some examples, the leads 212 are implanted on, within, or adjacent to a heart of a patient. The leads 212 may contain one or more electrodes 214 positioned at various locations on the leads 212, and in some cases at various distances from the housing 220. Some of the leads 212 may only include a single electrode 214, while other leads 212 may include multiple electrodes 214. Generally, the electrodes 214 are positioned on the leads 212 such that when the leads 212 are implanted within the patient, one or more of the electrodes 214 are positioned to perform a desired function. In some cases, the one or more of the electrodes 214 may be in contact with the patient's cardiac tissue. In some cases, the one or more of the electrodes 214 may be positioned substernally or subcutaneously but adjacent the patient's heart. In some cases, the electrodes 214 may conduct intrinsically generated electrical signals to the leads 212, e.g. signals representative of intrinsic cardiac electrical activity. The leads 212 may, in turn, conduct the received electrical signals to one or more of the modules 202, 204, 206, and 208 of the MD 200. In some cases, the MD 200 may generate electrical stimulation signals, and the leads 212 may conduct the generated electrical stimulation signals to the electrodes 214. The electrodes 214 may then conduct the electrical signals and delivery the signals to the patient's heart (either directly or indirectly).

The mechanical sensing module 208, as with the mechanical sensing module 108, may contain or be electrically connected to one or more sensors, such as accelerometers, blood pressure sensors, heart sound sensors, blood-oxygen sensors, acoustic sensors, ultrasonic sensors and/or other sensors which are configured to measure one or more mechanical/chemical parameters of the heart and/or patient. In some examples, one or more of the sensors may be located on the leads 212, but this is not required. In some examples, one or more of the sensors may be located in the housing 220.

While not required, in some examples, the MD 200 may be an implantable medical device. In such examples, the housing 220 of the MD 200 may be implanted in, for example, a transthoracic region of the patient. The housing 220 may generally include any of a number of known materials that are safe for implantation in a human body and may, when implanted, hermetically seal the various components of the MD 200 from fluids and tissues of the patient's body.

In some cases, the MD 200 may be an implantable cardiac pacemaker (ICP). In this example, the MD 200 may have one or more leads, for example leads 212, which are implanted on or within the patient's heart. The one or more leads 212 may include one or more electrodes 214 that are in contact with cardiac tissue and/or blood of the patient's heart. The MD 200 may be configured to sense intrinsically generated cardiac electrical signals and determine, for example, one or more cardiac arrhythmias based on analysis of the sensed signals. The MD 200 may be configured to deliver CRT, ΔTP therapy, bradycardia therapy, and/or other therapy types via the leads 212 implanted within the heart or in concert with the LCP by commanding the LCP to pace. In some examples, the MD 200 may additionally be configured provide defibrillation therapy.

In some instances, the MD 200 may be an implantable cardioverter-defibrillator (ICD). In such examples, the MD 200 may include one or more leads implanted within a patient's heart. The MD 200 may also be configured to sense cardiac electrical signals, determine occurrences of tachyarrhythmias based on the sensed signals, and may be configured to deliver defibrillation therapy in response to determining an occurrence of a tachyarrhythmia. In some instances, the MD 200 may be a subcutaneous implantable cardioverter-defibrillator (S-ICD). In examples where the MD 200 is an S-ICD, one of the leads 212 may be a subcutaneously implanted lead. In at least some examples where the MD 200 is an S-ICD, the MD 200 may include only a single lead which is implanted subcutaneously, but this is not required. In some cases, the S-ICD lead may extend subcutaneously from the S-ICD can, around the sternum and may terminate adjacent the interior surface of the sternum.

In some examples, the MD 200 may not be an implantable medical device. Rather, the MD 200 may be a device external to the patient's body, and may include skin-electrodes that are placed on a patient's body. In such examples, the MD 200 may be able to sense surface electrical signals (e.g. cardiac electrical signals that are generated by the heart or electrical signals generated by a device implanted within a patient's body and conducted through the body to the skin). In such examples, the MD 200 may be configured to deliver various types of electrical stimulation therapy, including, for example, defibrillation therapy. The MD 200 may be further configured to deliver electrical stimulation via the LCP by commanding the LCP to deliver the therapy.

Figure 3:
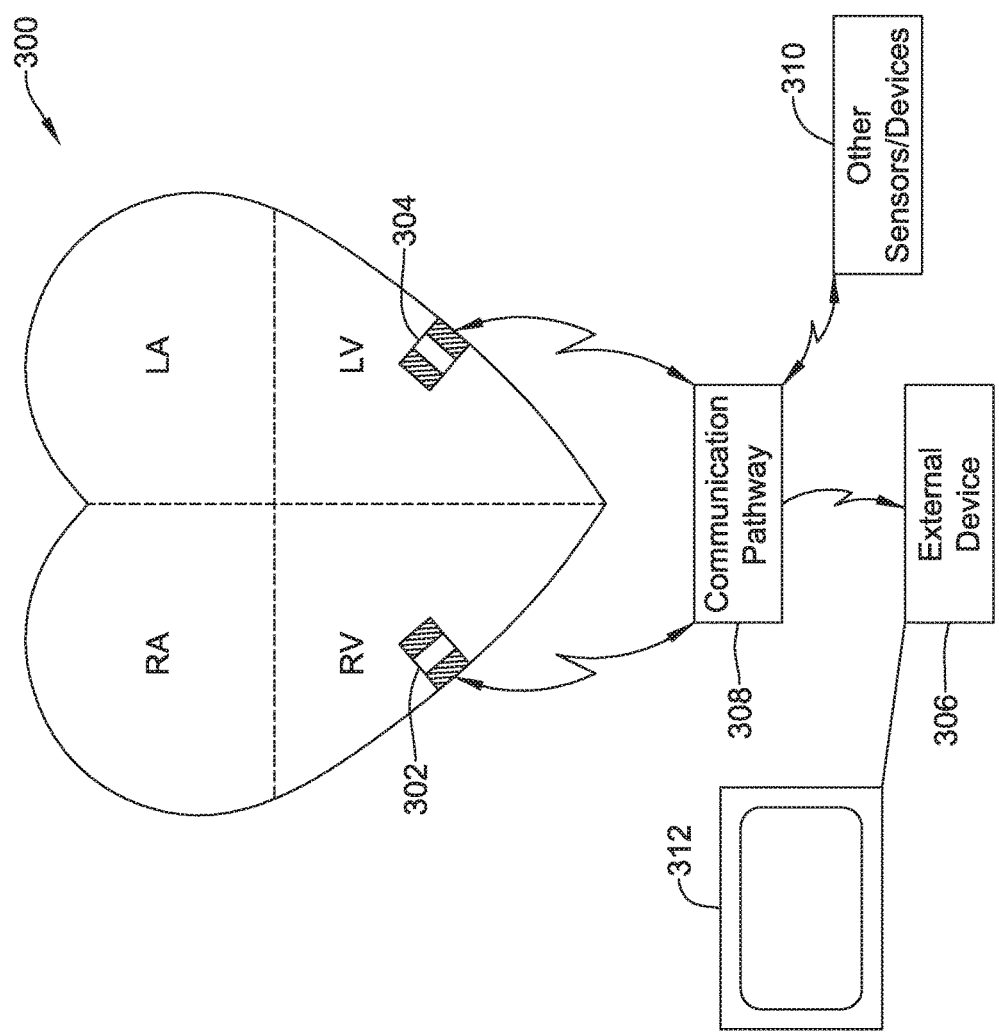
FIG. 3 is a schematic diagram of an exemplary medical system that includes multiple LCPs and/or other devices in communication with one another.

FIG. 3 shows an example medical device system with a communication pathway through which multiple medical devices 302, 304, 306, and/or 310 may communicate. In the example shown, the medical device system 300 may include LCPs 302 and 304, an external medical device 306, and other sensors/devices 310. The external device 306 may be any of the devices described previously with respect to MD 200. In some embodiments, the external device 306 may be provided with or be in communication with a display 312. The display 312 may be a personal computer, tablet computer, smart phone, laptop computer, or other display as desired. In some instances, the display 312 may include input means for receiving an input from a user. For example, the display 312 may also include a keyboard, mouse, actuatable (e.g. pushable) buttons, or a touchscreen display. These are just examples. The other sensors/devices 310 may be any of the devices described previously with respect to the MD 200. In some instances, the other sensors/devices 310 may include a sensor, such as an accelerometer or blood pressure sensor, or the like. In some cases, the other sensors/devices 310 may include an external programmer device that may be used to program one or more devices of the system 300.

Various devices of the system 300 may communicate via a communication pathway 308. For example, the LCPs 302 and/or 304 may sense intrinsic cardiac electrical signals and may communicate such signals to one or more other devices 302/304, 306, and 310 of the system 300 via the communication pathway 308. In one example, one or more of the devices 302/304 may receive such signals and, based on the received signals, determine an occurrence of an arrhythmia. In some cases, the device or devices 302/304 may communicate such determinations to one or more other devices 306 and 310 of the system 300. In some cases, one or more of the devices 302/304, 306, and 310 of the system 300 may take action based on the communicated determination of an arrhythmia, such as by delivering a suitable electrical stimulation to the heart of the patient. In another example, the LCPs 302 and/or 304 may sense indications of blood pressure (e.g. via one or more pressure sensors) and indications of volume (e.g. via an impedance between the electrodes of an LCP or between LCPs via an ultrasound transducer placed within the LCP, or via strain sensors placed on the heart in communication with the LCP). In one example, one or more of the devices 302/304 may receive such signals and, based on the received signals, determine a pressure-volume loop, and in some cases may communicate such information to one or more other devices 302/304, 306, and 310 of the system 300 via the communication pathway 308.

It is contemplated that the communication pathway 308 may communicate using RF signals, inductive coupling, conductive coupling optical signals, acoustic signals, or any other signals suitable for communication. Additionally, in at least some examples, the device communication pathway 308 may comprise multiple signal types. For instance, the other sensors/device 310 may communicate with the external device 306 using a first signal type (e.g. RF communication) but communicate with the LCPs 302/304 using a second signal type (e.g. conducted communication). Further, in some examples, communication between devices may be limited. For instance, as described above, in some examples, the LCPs 302/304 may communicate with the external device 306 only through the other sensors/devices 310, where the LCPs 302/304 send signals to the other sensors/devices 310, and the other sensors/devices 310 relay the received signals to the external device 306.

In some cases, the communication pathway 308 may include conducted communication. Accordingly, devices of the system 300 may have components that allow for such conducted communication. For instance, the devices of the system 300 may be configured to transmit conducted communication signals (e.g. current and/or voltage pulses) into the patient's body via one or more electrodes of a transmitting device, and may receive the conducted communication signals (e.g. pulses) via one or more electrodes of a receiving device. The patient's body may "conduct" the conducted communication signals (e.g. pulses) from the one or more electrodes of the transmitting device to the electrodes of the receiving device in the system 300. In such examples, the delivered conducted communication signals (e.g. pulses) may differ from pacing or other therapy signals. For example, the devices of the system 300 may deliver electrical communication pulses at an amplitude/pulse width that is sub-threshold to the heart. Although, in some cases, the amplitude/pulse width of the delivered electrical communication pulses may be above the capture threshold of the heart, but may be delivered during a refractory period of the heart and/or may be incorporated in or modulated onto a pacing pulse, if desired.

Delivered electrical communication pulses may be modulated in any suitable manner to encode communicated information. In some cases, the communication pulses may be pulse width modulated or amplitude modulated. Alternatively, or in addition, the time between pulses may be modulated to encode desired information. In some cases, conducted communication pulses may be voltage pulses, current pulses, biphasic voltage pulses, biphasic current pulses, or any other suitable electrical pulse as desired.

Figure 4:
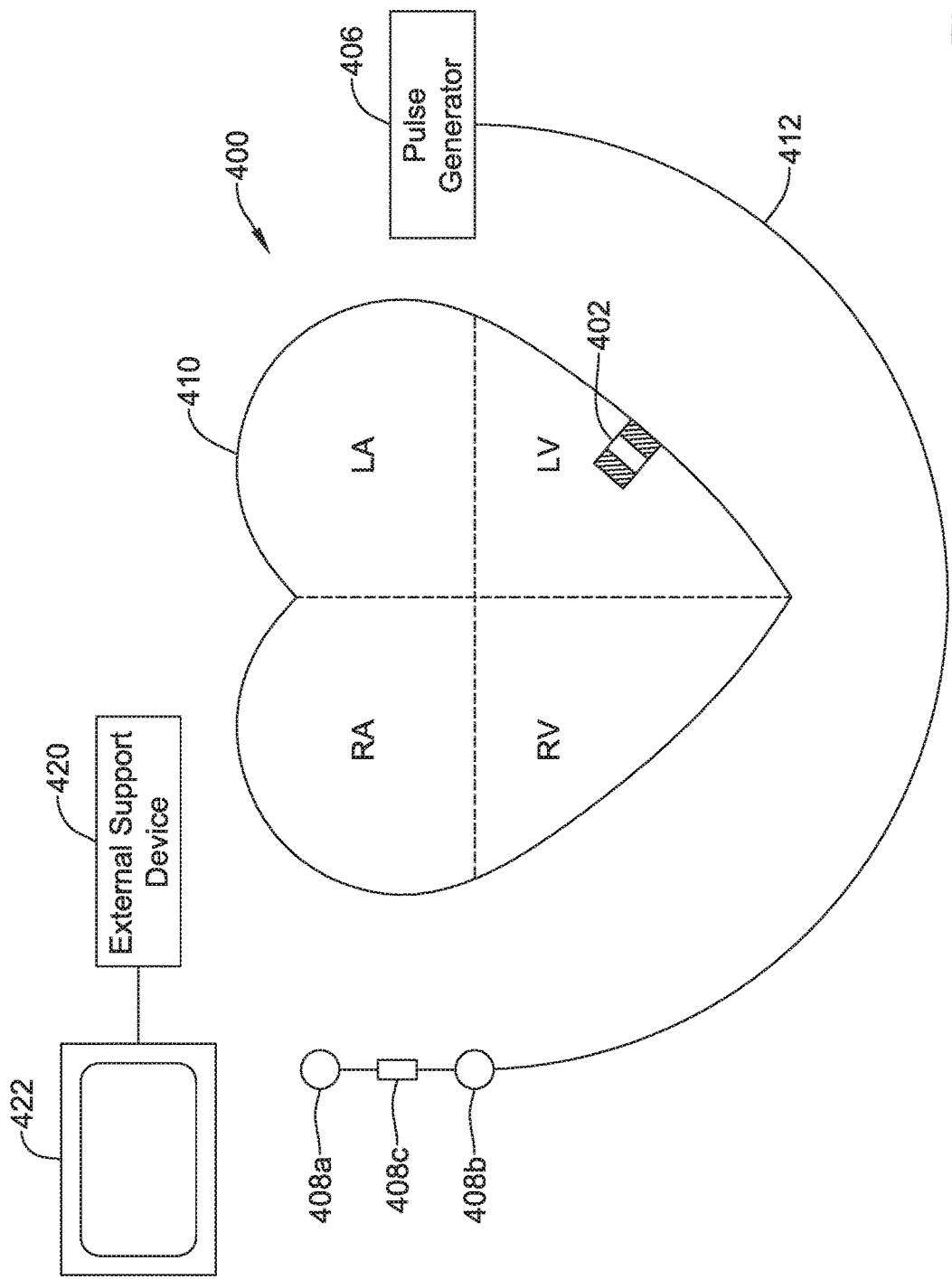
FIG. 4 is a schematic diagram of an exemplary medical system that includes an LCP and another medical device, in accordance with yet another example of the present disclosure.
Figure 5:
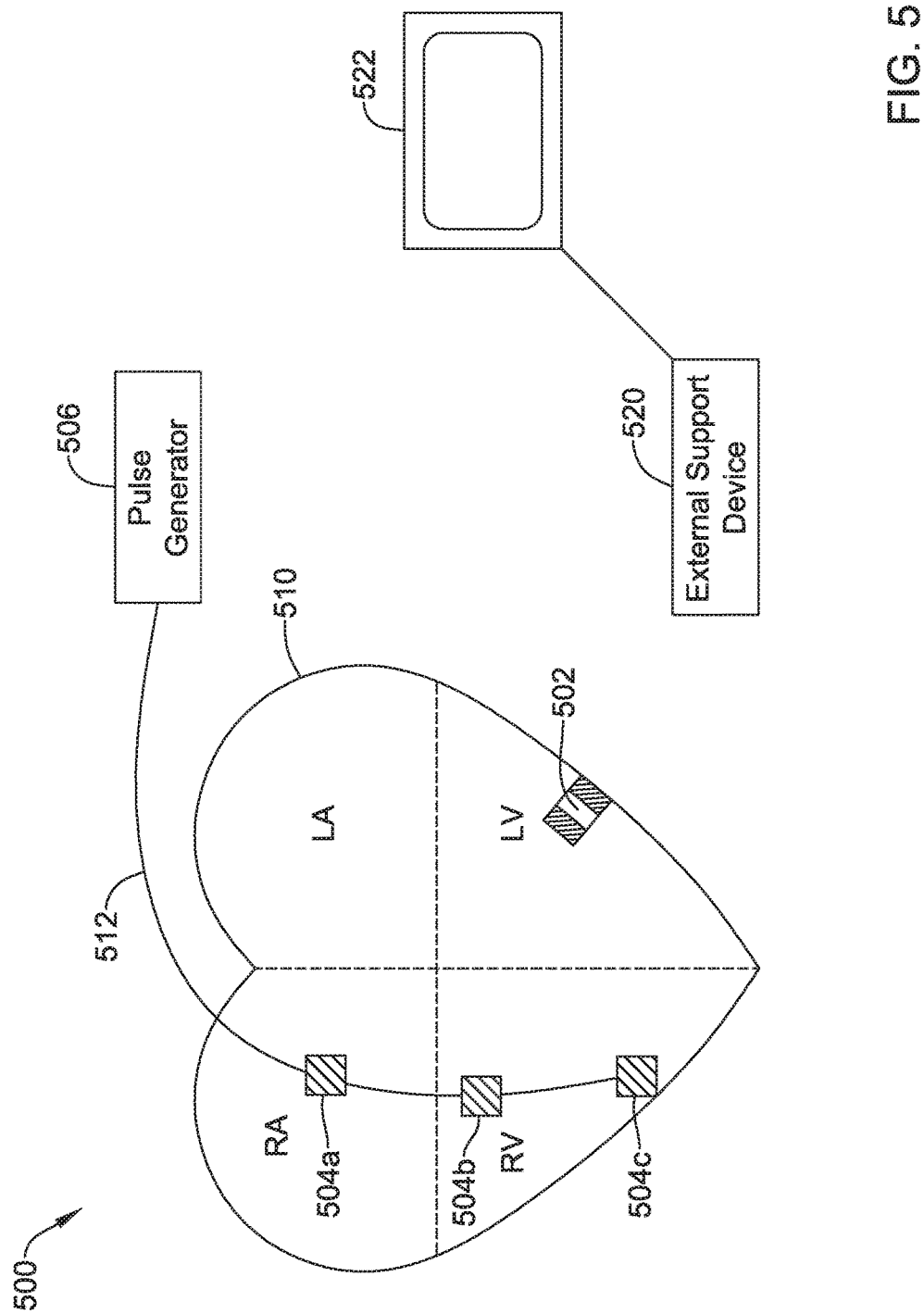
FIG. 5 is a schematic diagram of an exemplary medical system that includes an LCP and another medical device, in accordance with yet another example of the present disclosure.

FIGS. 4 and 5 show illustrative medical device systems that may be configured to operate according to techniques disclosed herein. In FIG. 4, an LCP 402 is shown fixed to the interior of the left ventricle of the heart 410, and a pulse generator 406 is shown coupled to a lead 412 having one or more electrodes 408a, 408b, 408c. In some cases, the pulse generator 406 may be part of a subcutaneous implantable cardioverter-defibrillator (S-ICD), and the one or more electrodes 408a, 408b, 408c may be positioned subcutaneously adjacent the heart. In some cases, the S-ICD lead may extend subcutaneously from the S-ICD can, around the sternum and one or more electrodes 408a, 408b, 408c may be positioned adjacent the interior surface of the sternum. In some cases, the LCP 402 may communicate with the subcutaneous implantable cardioverter-defibrillator (S-ICD).

In some cases, the LCP 402 may be in the right ventricle, right atrium or left atrium of the heart, as desired. In some cases, more than one LCP 402 may be implanted. For example, one LCP may be implanted in the right ventricle and another may be implanted in the right atrium. In another example, one LCP may be implanted in the right ventricle and another may be implanted in the left ventricle. In yet another example, one LCP may be implanted in each of the chambers of the heart.

In FIG. 5, an LCP 502 is shown fixed to the interior of the left ventricle of the heart 510, and a pulse generator 506 is shown coupled to a lead 512 having one or more electrodes 504a, 504b, 504c. In some cases, the pulse generator 506 may be part of an implantable cardiac pacemaker (ICP) and/or an implantable cardioverter-defibrillator (ICD), and the one or more electrodes 504a, 504b, 504c may be positioned in the heart 510. In some cases, the LCP 502 may communicate with the implantable cardiac pacemaker (ICP) and/or an implantable cardioverter-defibrillator (ICD).

The medical device systems 400 and 500 may also include an external support device, such as external support devices 420 and 520. The external support devices 420 and 520 can be used to perform functions such as device identification, device programming and/or transfer of real-time and/or stored data between devices using one or more of the communication techniques described herein. As one example, communication between the external support device 420 and the pulse generator 406 is performed via a wireless mode, and communication between the pulse generator 406 and the LCP 402 is performed via a conducted mode. In some examples, communication between the LCP 402 and the external support device 420 is accomplished by sending communication information through the pulse generator 406. However, in other examples, communication between the LCP 402 and the external support device 420 may be via a communication module. In some embodiments, the external support devices 420, 520 may be provided with or be in communication with a display 422, 522. The display 422, 522 may be a personal computer, tablet computer, smart phone, laptop computer, or other display as desired. In some instances, the display 422, 522 may include input means for receiving an input from a user. For example, the display 422, 522 may also include a keyboard, mouse, actuatable buttons, or be a touchscreen display. These are just examples.

FIGS. 4-5 illustrate two examples of medical device systems that may be configured to operate according to techniques disclosed herein. Other example medical device systems may include additional or different medical devices and/or configurations. For instance, other medical device systems that are suitable to operate according to techniques disclosed herein may include additional LCPs implanted within the heart. Another example medical device system may include a plurality of LCPs without other devices such as the pulse generator 406 or 506, with at least one LCP capable of delivering defibrillation therapy. In yet other examples, the configuration or placement of the medical devices, leads, and/or electrodes may be different from those depicted in FIGS. 4 and 5. Accordingly, it should be recognized that numerous other medical device systems, different from those depicted in FIGS. 4 and 5, may be operated in accordance with techniques disclosed herein. As such, the examples shown in FIGS. 4 and 5 should not be viewed as limiting in any way.

Figure 6:
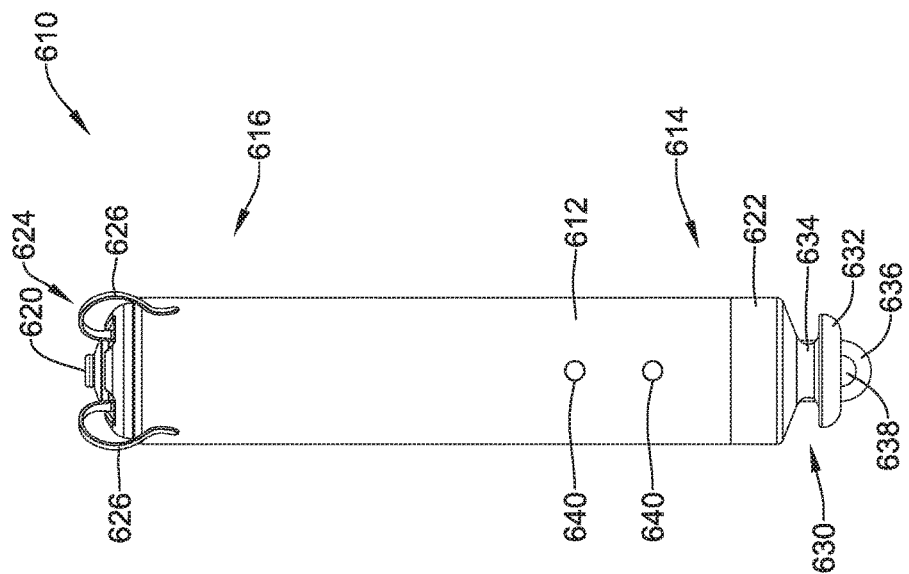
FIG. 6 is a side view of an illustrative implantable leadless cardiac pacing device.

FIG. 6 is a side view of an illustrative implantable leadless cardiac pacemaker (LCP) 610. The LCP 610 may be similar in form and function to the LCP 100 described above. The LCP 610 may include any of the modules and/or structural features described above with respect to the LCP 100 described above. The LCP 610 may include a shell or housing 612 having a proximal end 614 and a distal end 616. The illustrative LCP 610 includes a first electrode 620 secured relative to the housing 612 and positioned adjacent to the distal end 616 of the housing 612 and a second electrode 622 secured relative to the housing 612 and positioned adjacent to the proximal end 614 of the housing 612. In some cases, the housing 612 may include a conductive material and may be insulated along a portion of its length. A section along the proximal end 614 may be free of insulation so as to define the second electrode 622. The electrodes 620, 622 may be sensing and/or pacing electrodes to provide electro-therapy and/or sensing capabilities. The first electrode 620 may be capable of being positioned against or may otherwise contact the cardiac tissue of the heart while the second electrode 622 may be spaced away from the first electrode 620. The first and/or second electrodes 620, 622 may be exposed to the environment outside the housing 612 (e.g. to blood and/or tissue).

In some cases, the LCP 610 may include a pulse generator (e.g., electrical circuitry) and a power source (e.g., a battery) within the housing 612 to provide electrical signals to the electrodes 620, 622 to control the pacing/sensing electrodes 620, 622. While not explicitly shown, the LCP 610 may also include, a communications module, an electrical sensing module, a mechanical sensing module, and/or a processing module, and the associated circuitry, similar in form and function to the modules 102, 106, 108, 110 described above. The various modules and electrical circuitry may be disposed within the housing 612. Electrical communication between the pulse generator and the electrodes 620, 622 may provide electrical stimulation to heart tissue and/or sense a physiological condition.

In the example shown, the LCP 610 includes a fixation mechanism 624 proximate the distal end 616 of the housing 612. The fixation mechanism 624 is configured to attach the LCP 610 to a wall of the heart H, or otherwise anchor the LCP 610 to the anatomy of the patient. As shown in FIGS.

6, 7A and 7B, in some instances, the fixation mechanism 624 may include one or more, or a plurality of hooks or tines 626 anchored into the cardiac tissue of the heart H to attach the LCP 610 to a tissue wall. In other instances, the fixation mechanism 624 may include one or more, or a plurality of passive tines, configured to entangle with trabeculae within the chamber of the heart H and/or a helical fixation anchor configured to be screwed into a tissue wall to anchor the LCP 610 to the heart H. These are just examples.

The LCP 610 may further include a docking member 630 proximate the proximal end 614 of the housing 612. The docking member 630 may be configured to facilitate delivery and/or retrieval of the LCP 610. For example, the docking member 630 may extend from the proximal end 614 of the housing 612 along a longitudinal axis of the housing 612. The docking member 630 may include a head portion 632 and a neck portion 634 extending between the housing 612 and the head portion 632. The head portion 632 may be an enlarged portion relative to the neck portion 634. For example, the head portion 632 may have a radial dimension from the longitudinal axis of the LCP 610 that is greater than a radial dimension of the neck portion 634 from the longitudinal axis of the LCP 610. In some cases, the docking member 630 may further include a tether retention structure 636 extending from or recessed within the head portion 632. The tether retention structure 636 may define an opening 638 configured to receive a tether or other anchoring mechanism therethrough. While the retention structure 636 is shown as having a generally "U-shaped" configuration, the retention structure 636 may take any shape that provides an enclosed perimeter surrounding the opening 638 such that a tether may be securably and releasably passed (e.g. looped) through the opening 638. In some cases, the retention structure 636 may extend though the head portion 632, along the neck portion 634, and to or into the proximal end 614 of the housing 612. The docking member 630 may be configured to facilitate delivery of the LCP 610 to the intracardiac site and/or retrieval of the LCP 610 from the intracardiac site. While this describes one example docking member 630, it is contemplated that the docking member 630, when provided, can have any suitable configuration.

It is contemplated that the LCP 610 may include one or more pressure sensors 640 coupled to or formed within the housing 612 such that the pressure sensor(s) is exposed to and/or otherwise operationally coupled with the environment outside the housing 612 to measure blood pressure within the heart. In some cases, the pressure sensor 640 may be coupled to an exterior surface of the housing 612. In other cases, the pressures sensor 640 may be positioned within the housing 612 with a pressure acting on the housing and/or a port on the housing 612 to affect the pressure sensor 640. For example, if the LCP 610 is placed in the left ventricle, the pressure sensor(s) 640 may measure the pressure within the left ventricle. If the LCP 610 is placed in another portion of the heart (such as one of the atriums or the right ventricle), the pressures sensor(s) may measure the pressure within that portion of the heart. The pressure sensor(s) 640 may include a MEMS device, such as a MEMS device with a pressure diaphragm and piezoresistors on the diaphragm, a piezoelectric sensor, a capacitor-Micro-machined Ultrasonic Transducer (cMUT), a condenser, a micromanometer, or any other suitable sensor adapted for measuring cardiac pressure. The pressures sensor(s) 640 may be part of a mechanical sensing module described herein. It is contemplated that the pressure measurements obtained from the pressures sensor(s) 640 may be used to generate a pressure curve over cardiac cycles. The pressure readings may be taken in combination with a cardiac chamber volume measurement such as impedance measurements (e.g. the impedance between electrodes 620 and 622) to generate a pressure-impedance loop for one or more cardiac cycles as will be described in more detail below. The impedance may be a surrogate for chamber volume, and thus the pressure-impedance loop may be representative of a pressure-volume loop for the heart H.

In some embodiments, the LCP 610 may be configured to measure impedance between the electrodes 620, 622. More generally, the impedance may be measured between other electrode pairs, such as the additional electrodes 114' described above. In some cases, the impedance may be measured between two spaced LCP's, such as two LCP's implanted within the same chamber (e.g. LV) of the heart H, or two LCP's implanted in different chambers of the heart H (e.g. RV and LV). The processing module of the LCP 610 and/or external support devices may derive a measure of cardiac volume from intracardiac impedance measurements made between the electrodes 620, 622 (or other electrodes). Primarily due to the difference in the resistivity of blood and the resistivity of the cardiac tissue of the heart H, the impedance measurement may vary during a cardiac cycle as the volume of blood (and thus the volume of the chamber) surrounding the LCP changes. In some cases, the measure of cardiac volume may be a relative measure, rather than an actual measure. In some cases, the intracardiac impedance may be correlated to an actual measure of cardiac volume via a calibration process, sometimes performed during implantation of the LCP(s). During the calibration process, the actual cardiac volume may be determined using fluoroscopy, ultrasound, or the like, and the measured impedance may be correlated to the actual cardiac volume. Additionally or alternatively, the cardiac volume may be determined via ultrasound measurements and correlated to the impedance measurement one or more times after implantation of the LCP 610. In some embodiments the pressure sensor measurement from LCP 610 can be communicated to another implanted device (e.g. pulse generator 406) or external device (e.g. external device 306) which has the cardiac volume measurement.

In some cases, the LCP 610 may be provided with energy delivery circuitry operatively coupled to the first electrode 620 and the second electrode 622 for causing a current to flow between the first electrode 620 and the second electrode 622 in order to determine the impedance between the two electrodes 620, 622 (or other electrode pair). It is contemplated that the energy delivery circuitry may also be configured to deliver pacing pulses via the first and/or second electrodes 620, 622. The LCP 610 may further include detection circuitry operatively coupled to the first electrode 620 and the second electrode 622 for detecting an electrical signal received between the first electrode 620 and the second electrode 622. In some instances, the detection circuitry may be configured to detect cardiac signals received between the first electrode 620 and the second electrode 622.

When the energy delivery circuitry delivers a current between the first electrode 620 and the second electrode 622, the detection circuitry may measure a resulting voltage between the first electrode 620 and the second electrode 622 (or between a third and fourth electrode separate from the first electrode 620 and the second electrode 622) to determine the impedance. When the energy delivery circuitry delivers a voltage between the first electrode 620 and the second electrode 622, the detection circuitry may measure a resulting current between the first electrode 620 and the second electrode 622 (or between a third and fourth electrode separate from the first electrode 620 and the second electrode 622) to determine the impedance.

In some embodiments, the impedance may be measured between electrodes on different devices and/or in different heart chambers. For example, impedance may be measured between a first pair of electrodes in the left ventricle and a second pair of electrodes in the right ventricle. This may be achieved by injecting the current between the first pair of electrodes in one of the ventricles and measuring the resulting voltage in the second pair of electrodes in the other ventricle. In another example, impedance may be measured between a first pair of electrodes of a first LCP in the left ventricle and a second pair of electrodes of a second LCP in the left ventricle. In yet another example, impedance may be measured using a current injected by a different device. For example, a medical device (such as, but not limited to an S-ICD), may inject a known current into the heart and the LCP implanted in the heart H may measure a voltage resulting from the injected current to determine the impedance. These are just some examples. In yet another embodiment the volume measurement is provided by another medical device as an impedance-based measurement performed by an S-ICD and communicated to the LCP 610.

Figure 7A:
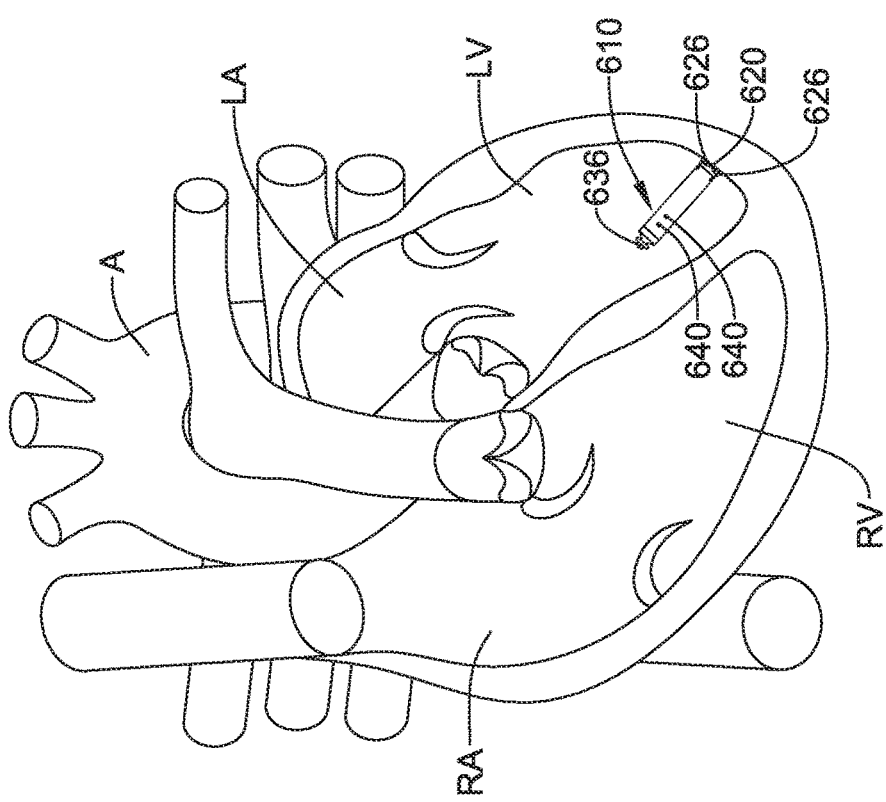
FIG. 7A is a plan view of an example leadless cardiac pacing device implanted within a heart during ventricular filling.
Figure 7B:
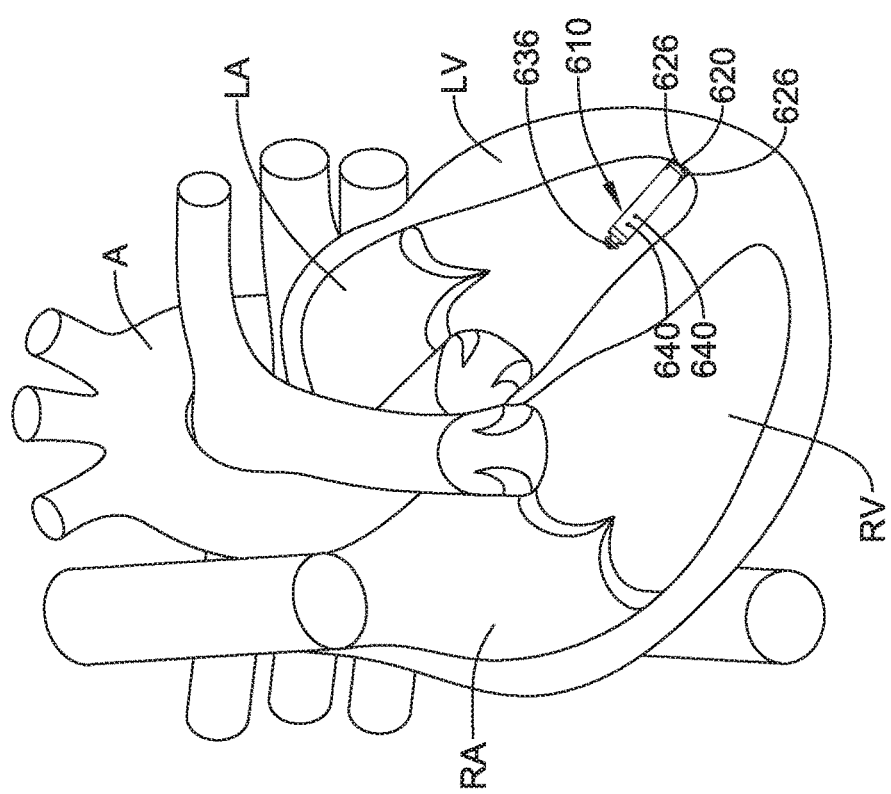
FIG. 7B is a plan view of an example leadless cardiac pacing device implanted within a heart during ventricular contraction.

FIG. 7A is a plan view of the example leadless cardiac pacing device 610 implanted within a left ventricle LV of the heart H during ventricular filling. The right ventricle RV, right atrium RA, left atrium LA, and aorta A are also illustrated. FIG. 7B is a plan view of the leadless cardiac pacing device 610 implanted within a left ventricle of the heart H during ventricular contraction. These figures illustrate how the volume of the left ventricle may change over a cardiac cycle. As can be seen in FIGS. 7A and 7B, the volume of the left ventricle during ventricular filling is larger than the volume of the left ventricle of the heart during ventricular contraction.

In some cases, the processing module and/or other control circuitry may capture, at a time point within each of one or more cardiac cycles, an impedance between the first electrode 620 and the second electrode 622 and a corresponding pressure within the heart (e.g. left ventricle), resulting in one or more impedance-pressure data pairs. These one or more data pairs may be used, in combination with other impedance-pressure data pairs taken at different times during the one or more cardiac cycles, to generate a pressure-volume loop. In some cases, one or more parameters may be extracted or derived from the pressure-volume loop. In any event, the pressure-volume loop may facilitate cardiac resynchronization therapy (CRT), patient health status monitoring, and/or the management of a non-CRT cardiac therapy.

Figure 8:
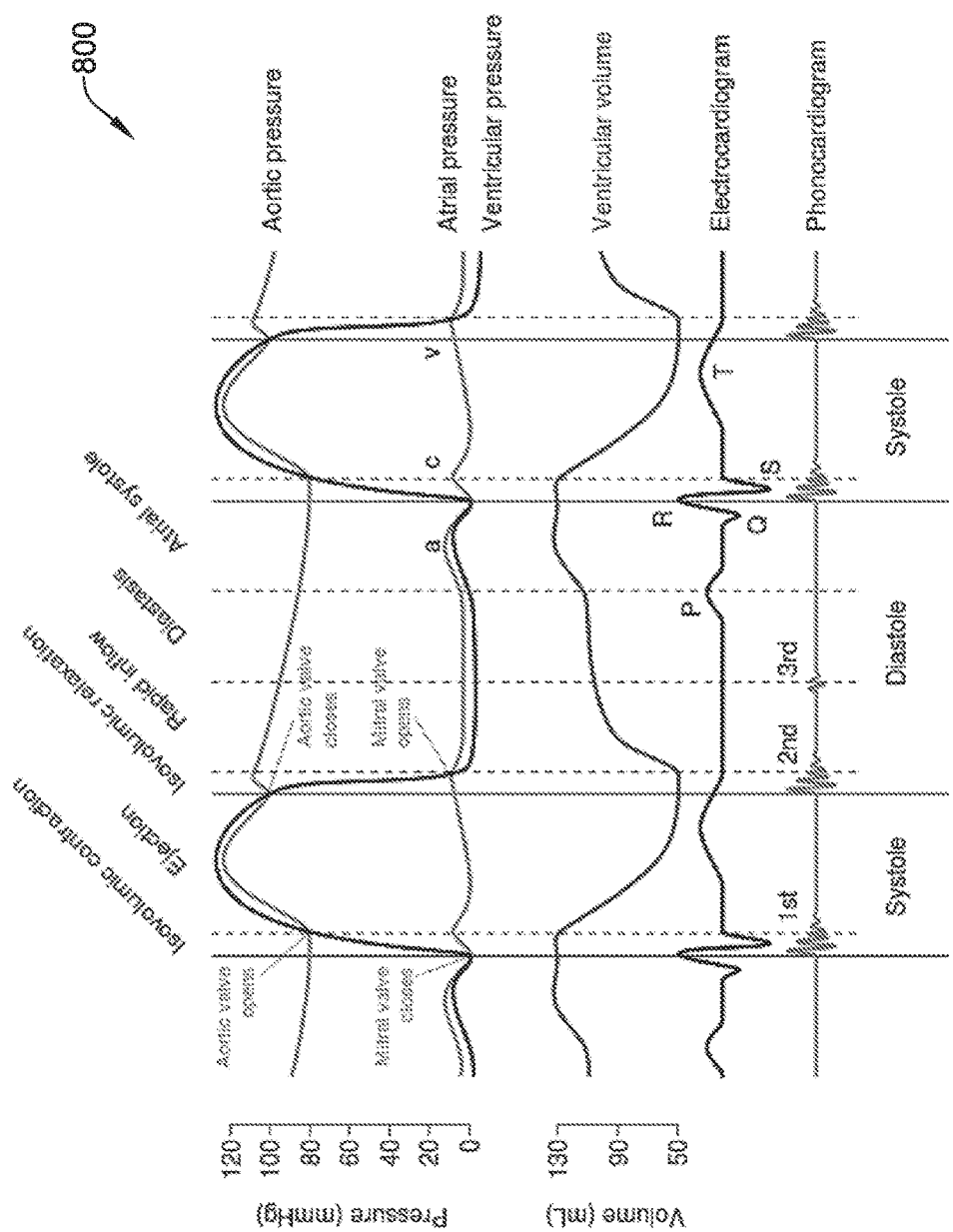
FIG. 8 is a graph showing example pressures and volumes within the heart over time.

FIG. 8 is a graph 800 showing example pressures and volumes within a heart over time. More specifically, FIG. 8 depicts the aortic pressure, left ventricular pressure, left atrial pressure, left ventricular volume, an electrocardiogram (ECG or egram), and heart sounds of the heart H. A cardiac cycle may begin with diastole, and the mitral valve opens. The ventricular pressure falls below the atrial pressure, resulting in the ventricular filling with blood. During ventricular filling, the aortic pressure slowly decreases as shown. During systole, the ventricle contracts. When ventricular pressure exceeds the atrial pressure, the mitral valve closes, generating the S1 heart sound. Before the aortic valve opens, an isovolumetric contraction phase occurs where the ventricle pressure rapidly increases but the ventricular volume does not significantly change. Once the ventricular pressure equals the aortic pressure, the aortic valve opens and the ejection phase begins where blood is ejected from the left ventricle into the aorta. The ejection phase continues until the ventricular pressure falls below the aortic pressure, at which point the aortic valve closes, generating the S2 heart sound. At this point, the isovolumetric relaxation phase begins and ventricular pressure falls rapidly until it is exceeded by the atrial pressure, at which point the mitral valve opens and the cycle repeats. Cardiac pressure curves for the pulmonary artery, the right atrium, and the right ventricle, and the cardiac volume curve for the right ventricle, similar to those illustrated in FIG. 8 for the left part of the heart, may be likewise generated. Typically, the cardiac pressure in the right ventricle is lower than the cardiac pressure in the left ventricle.

In one example, the heart sound signals can be recorded using acoustic sensors, (for example, a microphone), which capture the acoustic waves resulted from heart sounds. In another example, the heart sound signals can be recorded using accelerometers or pressure sensors that capture the accelerations or pressure waves caused by heart sounds. The heart sound signals can be recorded within or outside the heart. These are just examples.

FIG. 9A illustrates a method of representing pressure and volume parameters of the heart in a pressure-volume (PV) loop. PV loops can be used to determine performance characteristics of the heart. An illustrative PV loop 900 shows a normal PV characteristics for the left ventricle of the heart. The PV loop 900 moves in a counter-clockwise direction. The mitral valve opens at 904 and ventricular filling occurs along 902. The closure of the mitral valve causes the S1 heart sound at 906. Ventricular filling 902 ends at the point 906 with closure of the mitral valve. The point 906 represents the end diastolic volume (EDV) or the volume of blood in the heart at the end of its dilatation phase. The ventricle contracts at 906. Before the aortic valve opens at 910, an isovolumetric contraction phase occurs along 908 where the ventricle pressure rapidly increases but the ventricle volume does not significantly change. The ejection phase 912 lasts from point 910 until the aortic valve closes at the point 914. The closure of the aortic valve at point 914 generates the S2 heart sound, and also marks the end systolic volume (ESV), or the volume of blood in the heart at the end of its contraction phase. The isovolumetric relaxation phase 916 begins at the point 914 and continues until the mitral valve opens at point 904 and the cardiac cycle repeats. The PV loop 900 can be approximated if the points 904, 906, 910, and 914 (the four "corners" of the PV loop) are known.

The contractility index represents the capacity of the muscle to become shorter in response to a suitable stimulus. A measure of the contractility index can be estimated by calculating the slope of the end systolic pressure-volume line (shown as 918). A measure of the stroke work can be estimated by the area of the PV loop 900. A measure of the stroke volume can be estimated by the EDV minus the ESV, and represents the amount of blood ejected from the heart with each heartbeat. A measure of cardiac output can be estimated by multiplying the heart rate by the stroke volume. A measure of the ejection fraction (the proportion of the volume of blood in the ventricles at the end of diastole that is ejected during systole) can be estimated by the stroke volume divided by the EDV. These are only illustrative, and it is contemplated that other parameters may also be extracted or derived from the PV loop 900.

Figure 9B:
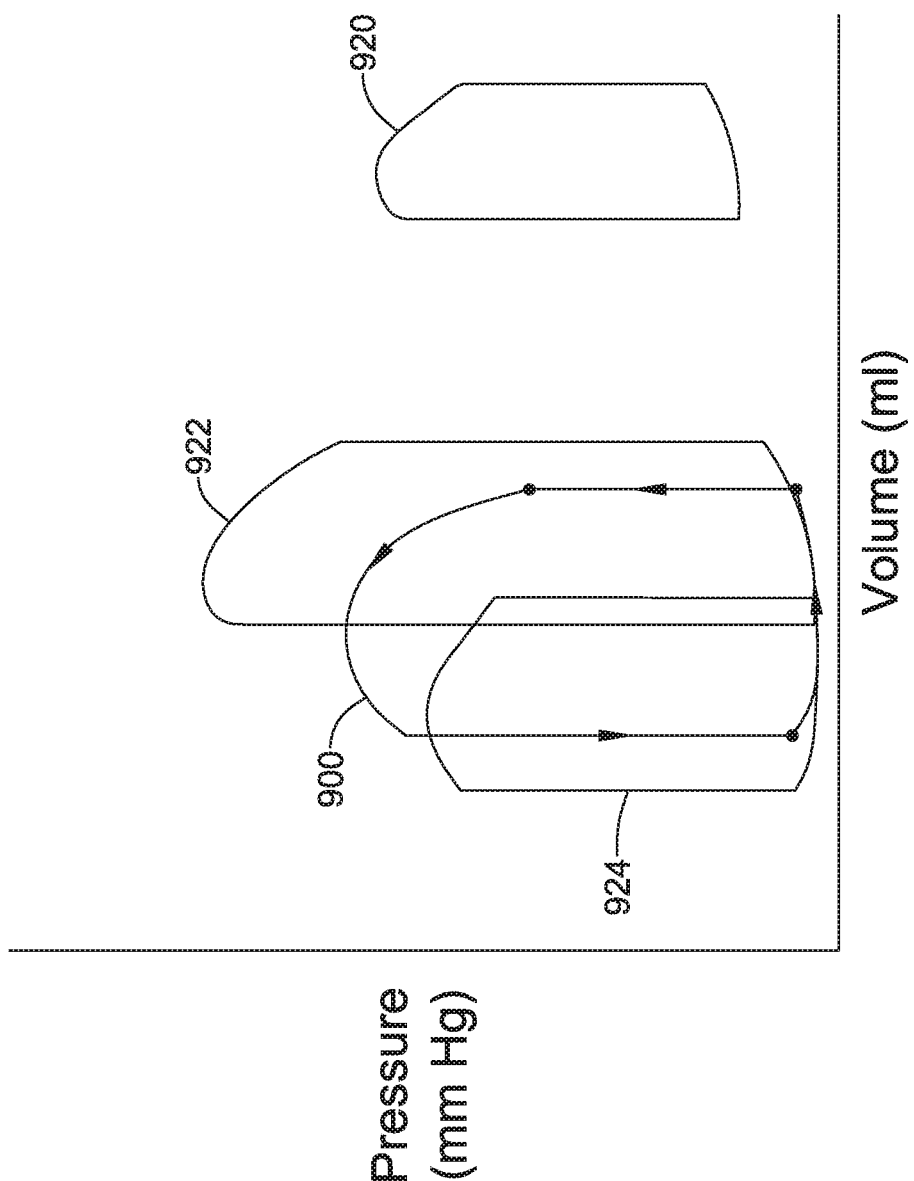

FIG. 9B illustrates how a variety of abnormalities in the heart may result in changes in a PV loop. PV loop 920 is representative of congestive heart failure. The PV loop 920 is shifted to the right of the normal PV loop 900. The PV loop 920 also has a substantially smaller stroke volume than the stroke volume of the normal PV loop 900 and lower peak pressure than the PV loop 900. The PV loop 922 is representative of aortic stenosis. The stroke volume is reduced and the ESV is increased compared to the normal PV loop 900. Mitral stenosis is represented by PV loop 924. In this case, the ESV increases slightly while the EDV is decreased, as is the stroke volume. Additional abnormal cardiac conditions can be identified using the PV loop.

FIGS. 9C-9F illustrate changes that may occur in the PV loop as the heart rate increases. FIG. 9C depicts a PV loop 926 at a heart rate of 72 beats per minute ("bpm"). FIGS. 9D and 9E depict PV loops 928, 930 at heart rates of 102 bpm and 150 bpm, respectively. FIG. 9F depicts a PV loop 932 at a heart rate of 180 bpm. As shown in FIG. 9F, the PV loop 932 is narrowing, indicating a decrease in the stroke volume and corresponding decrease in the volume of blood ejected from the heart. As the heart rate increases beyond 180 bpm, such as during fibrillation, the PV loop may continue to shrink until it resembles a dot or small square.

As can be seen in FIGS. 9A-9F, a pressure volume loop can provide a clinician with details regarding the heart's function. As such, and as described above, it may be desirable to capture and record data relating to the pressure and volume of various chambers of the heart (e.g. the left ventricle), sometimes over time. For example, the processing module and/or other control circuitry of any of the above described LCP devices 100, 302, 304, 402, 502, 610 may be configured to determine a new pressure volume loop every minute, hour, day, week, month, or during a doctor visit. The previous pressure volume loop may be stored for later use, such as to identify a change and/or trend. In some cases, the LCP device may store the pressure volume loops. In some cases, the LCP may transmit the pressure volume loops to another device, such as an S-ICD device or a remote device, to store the pressure volume loops. In some instances, the LCP/S-ICD/remote device may process the PV loop to extract features that more explicitly point to a particular physiologic or pathophysiologic condition of interest. One such feature is the slope of the line joining the upper-left corner of the loop to the origin, which is indicative of cardiac contractility. Features could include areas of certain portions of the loop or shape characteristics of certain portions of the loop. The pressure-volume loop(s) and/or the extracted features may facilitate cardiac rhythm therapy (CRT), patient health status monitoring, and/or the management of a non-CRT cardiac therapy. In some embodiments the pressure volume loop measurement and storage may be triggered by an event such as a medical condition occurrence (e.g. an arrhythmia), a worsening of a prior existing condition (e.g. heart failure decompensation), a time of day, an activity level, an initiation or change of therapy (e.g. device or drug), a heart rate, a respiration rate, and/or a patient action.

While an LCP may be used to collect the pressure and impedance pairs as described above, it is contemplated that a diagnostic device may be used that has no pacing capabilities. The diagnostic device may include two or more electrodes for measuring an impedance and/or for communicating with an LCP, S-ICD, or other device, and a one or more pressure sensors. The diagnostic device may be implanted within a chamber of the heart H. In some cases, a diagnostic device and LCP, both implanted in the same chamber, may cooperate to collect the pressure and impedance pairs. For example, the diagnostic device may collect the pressure information, while an LCP may collect the impedance information. When so provided, the LCP does not need a pressure sensor. The diagnostic device and LCP may synchronize the taking of the pressure and impedance information to result in pressure-impedance pairs. As described above the impedance may be correlated to blood volume in a chamber and/or used as a surrogate for a volume measurement to determine the volume of the blood in a chamber or the volume of the chamber. In some instances, a pressure-impedance loop may be generated with the obtained pressure-impedance data pairs in place of, or in addition to, a pressure-volume loop.

Figure 10:
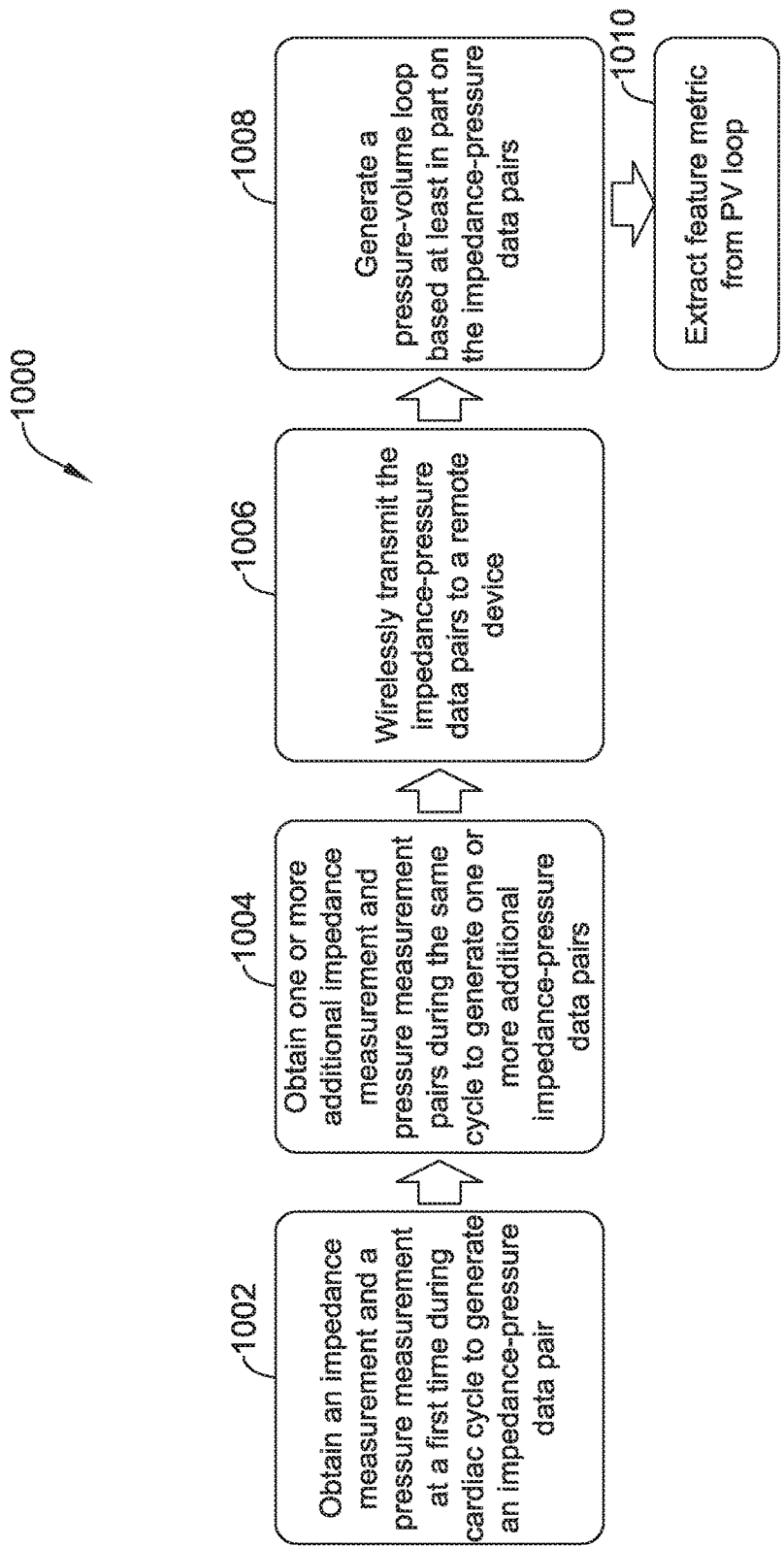
FIG. 10 is a flow diagram of an illustrative method for generating a pressure-volume loop for a ventricle of a human heart.

FIG. 10 is a flow chart of an illustrative method 1000 for generating a pressure-volume loop from data obtained from an implanted LCP such as any of the above described LCP devices 100, 302, 304, 402, 502, 610. While the method is described using an LCP, it is contemplated that other devices and/or combinations of devices may be used. For example, two or more LCPs may be used to collect data from different chambers in the heart. As described above, the LCP may include a processing module that includes control circuitry configured to control the operation of the LCP. In some instances, the processing module may include separate circuits for therapy delivery, hemodynamic (e.g. pressure) sensing, and/or volume sensing, although this is not required. It is contemplated that the processing module may further include an additional circuit or algorithm generating a PV loop which may be configured to convert the data obtained from one or more pressure sensors of the LCP and the impedance data obtained from the two or more electrodes into a PV loop.

As shown at block 1002, the processing module and/or any other circuits or sub-circuits of one or more LCPs (and/or other implantable devices) may obtain an impedance measurement and a pressure measurement simultaneously, or substantially simultaneously, at a first time during a cardiac cycle, resulting in a first impedance-pressure data pair. In some instances, the first time may correspond with an S1 heart sound, although this is not required. The data pair may be stored in a memory of the LCP. In some instances, the data pair may be stored in a table. In some cases, the data pair may be transmitted to a remote device, such as another LCP, an S-ICD device, or an external device. The processing module may then obtain one or more additional impedance-pressure measurement pairs at different times during the same cardiac cycle, as shown at block 1004. For example, a second impedance-pressure data pair may be determined at a second time, a third impedance-pressure data pair may be determined at a third time, a fourth impedance-pressure data pair may be determined at a fourth time, etc. In some instances, the second time may correspond with an S2 heart sound, although this is not required. The one or more additional data pairs may be stored in the memory of the LCP. In some cases, the LCP may transmit the impedance-pressure data pairs to another device, such as an S-ICD device or an external device. It is contemplated that the processing module may be configured to sample impedance-pressure data pairs at set time intervals or to obtain a predetermined number of impedance-pressure data pairs per cardiac cycle. It is contemplated that increasing the frequency of sampling may result in a more accurate PV loop. However, frequent sampling may decrease the life of the battery of the LCP(s). The use of the terms "first time" and "second time" are not intended to chronologically limit the order the impedance-pressure data pairs are obtained. In some instances, the circuitry may be configured to determine, at a plurality of times between the first time and the second time, a plurality of corresponding impedances between the first electrode and the second electrode and also corresponding pressures via the pressure sensor, resulting in a plurality of additional impedance-pressure data pairs.

Once the LCP has gathered impedance-pressure data pairs over at least one cardiac cycle, the data pairs may be converted into a PV loop, as shown at block 1008. For example, the LCP or an external device may be configured to generate a PV loop that is based, at least in part, on the plurality of data pairs. In some embodiments, the processing module and/or external device may be configured to generate a pressure-impedance (PZ) loop instead of a PV loop. The PZ loop may provide similar information as the PV loop but may require less processing. At a high level, the PZ loop may be considered equivalent to the PV loop.

It is contemplated that data pairs obtained over a plurality (e.g. two or more, five or more, ten or more) of cardiac cycles may be averaged to generate the PV loop. For example, the LCP circuitry may be configured to record or sample pressure and impedance data at the same (or similar) time points in each in a series of cardiac cycles such that the first impedance-pressure data pair from a first cardiac cycle can be averaged with the corresponding first impedance-pressure data pair from any number of subsequent (or preceding) cardiac cycles. Averaging the data over a plurality of cardiac cycles may reduce the noise and provide a more robust representation of the PV loop.

In some instances, the processing module may include circuitry to convert the data pairs into a PV loop. In other instances, the LCP circuitry may be configured to wirelessly transmit the first impedance-pressure data pair (and/or any additional data pairs) to a remote or external device, such as, but not limited to, any of the medical or external devices described above, as shown at block 1006. The LCP may communicate with the remote or external device via radiofrequency (RF) signals, inductive coupling, optical signals, acoustic signals, conducted communication signals, and/or any other signals suitable for communication.

Various metrics may be extracted from the PV loop, as desired, as shown at block 1010. For example, the loop area and loop width. A measure of the contractility index of the heart can be estimated by calculating the slope of the end systolic pressure-volume line. A measure of the stroke work can be estimated by the area of the loop. A measure of the stroke volume can be estimated by the EDV minus the ESV of the loop. A measure of the ejection fraction can be estimated by the stroke volume divided by the EDV. These are only illustrative, and it is contemplated that other metrics may also be extracted or derived from the loop.

It is contemplated that the PV loop and/or the extracted metrics may be used to optimize therapies and/or provide the clinician with information regarding cardiac functionality. For example, the PV loop and/or extracted metrics may be used to change the AV delay when pacing, the electrodes used for pacing and/or sensing, pacing timing, and/or optimization of CRT and non-CRT therapies, etc. In some cases, it is contemplated that when the PV loop is generated within the processing module of the LCP, the processing module may be programmed to optimize CRT therapies with or without a clinician viewing the PV loop.

In some instances, the pressure-impedance data pairs may be transmitted from the LCP to a remote device, such as an S-ICD device, an external device or other device. It is contemplated that the remote device may extract various metrics from the pressure-impedance data pairs, and communicate information to the LCP to improve CRT and/or non-CRT therapies delivered by the LCP.

Figure 11:
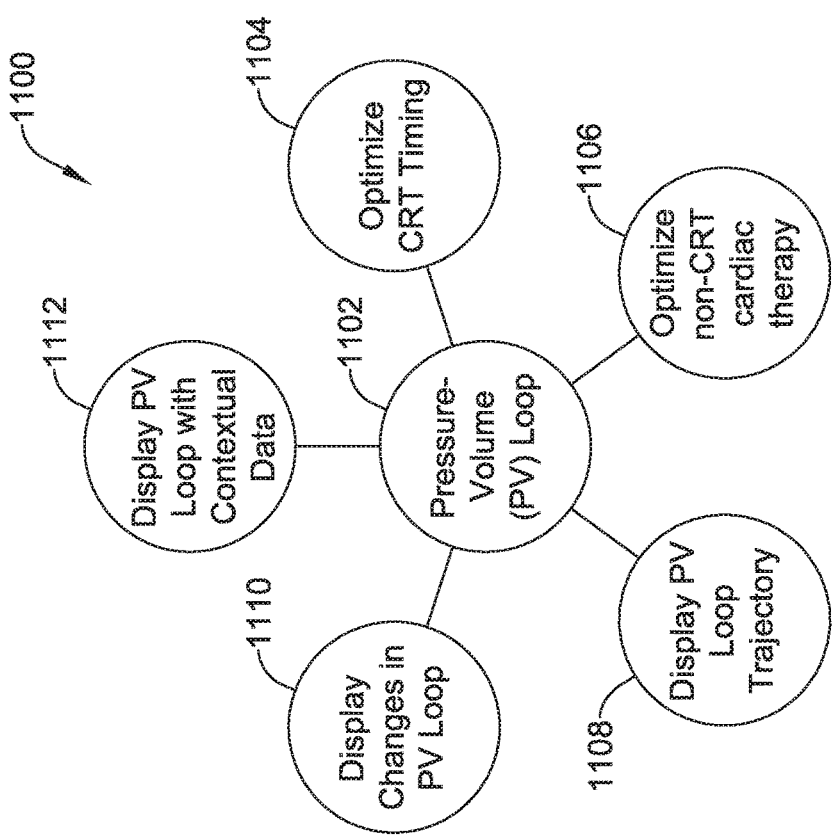
FIG. 11 is a diagram illustrating the various uses of a pressure-volume loop for the ventricle.

FIG. 11 is a diagram 1100 illustrating some, but not all, potential uses of one or more PV loops 1102 sampled to one or more LCP's. The PV loop 1102 may provide information that allows a clinician to optimize CRT timing 1104. For example, the edges and volume of a PV loop 1102 may vary with the CRT timing. In some cases, these changes in the PV loop 1102 may allow a clinician to identify proper CRT timing parameters. In some cases, these changes in the PV loop 1102 may allow a clinician to identify pacing sites as not acceptable, acceptable, better, or best. In an implant with multiple electrodes (e.g. a multi-electrode LCP or multiple LCPs), multiple pacing sites may be available. The PV loop may allow the clinician to identify and use the best pacing sites. Additionally, or alternatively, the PV loop may also allow a clinician to optimize non-CRT cardiac therapy 1106 (e.g. effectiveness or dose of ACE inhibitors, diuretics, etc.).

In some instances, a device (e.g. LCP, external device, S-ICD, etc.) may be configured to measure specific features of the loop. For instance, based on one sensor, paired measurements on the other sensor may be triggered at just the falling and rising edges of the loop, or at just the "corners" of the loop, depending on what cardiac parameters are of most interest. This may save data capacity, processing capacity, battery energy, and preserve or enhance accuracy at relevant portions of the PV loop and/or PZ loop. This is just an example. Other loop sampling strategies may be employed to capture different portions of the PV loop and/or PZ loop, as desired. The loop sampling strategy can be programmable by external unit and/or varied according to internal algorithms.

In some instances, multiple PV loops generated from different cardiac cycles (or different average cardiac cycles) may be displayed simultaneously to display and/or illustrate a PV loop trajectory or trend 1108. In other words, the LCP and/or remote device may be configured to store and display a plurality of PV loops generated over a period of time. The PV loop trajectory 1108 may allow a clinician to view the effectiveness of a therapy (CRT and/or non-CRT). For example, a PV loop trajectory 1108 may allow a clinician to see changes in the PV loop after a drug change (dosage or type), a CRT timing change, an AV delay change, other therapy change, etc. A PV loop trajectory 1108 may also allow a clinician to determine or if there are changes not associated with a therapy change that might indicate changes in a current therapy or a new therapy are needed, such as decompensation of the heart H. The PV loop trajectory 1108 may also be used to guide patient lifestyle changes.

Multiple PV loops generated from different cardiac cycles (or different average cardiac cycles) may be compared to one another to determine and display changes in the PV loop 1110. Some illustrative changes in the PV loop may include, but are not limited to horizontal (e.g. width), vertical (e.g. height), area, slope, etc. It is further contemplated that a PV loop 1102 may be displayed with contextual data 1112. Contextual data may include, but is not limited to patient metabolic demands, activity level (e.g. active, inactive), posture (sitting, standing, lying down, etc.), sleep status, etc. This data may be captured along with each of the pressure-impedance data pairs. In some cases, the LCP may be configured to record a patent's metabolic demands, activity level, or other contextual data.

In some instances, the LCP may be in wireless communication with an external wearable device, such as an activity tracker (e.g. iWatch®, FitBit®, etc.), that may provide contextual information such as sleep status and/or activity level. It is contemplated that the generated PV loops may be processed or grouped according to context. For example, PV loops may be processed according to time of day, posture, activity level, metabolic demands, heart rate range, etc.

Those skilled in the art will recognize that the present disclosure may be manifested in a variety of forms other than the specific examples described and contemplated herein. For instance, as described herein, various examples include one or more modules described as performing various functions. However, other examples may include additional modules that split the described functions up over more modules than that described herein. Additionally, other examples may consolidate the described functions into fewer modules. Accordingly, departure in form and detail may be made without departing from the scope and spirit of the present disclosure as described in the appended claims.

What is claimed is:

1. A leadless cardiac pacemaker (LCP) configured to sense cardiac activity and to pace a patient's heart, the LCP comprising:
    a housing;
    a first electrode secured relative to the housing and exposed to the environment outside of the housing;
    a second electrode secured relative to the housing and exposed to the environment outside of the housing, the second electrode is spaced from the first electrode;
    a pressure sensor secured relative to the housing and is coupled to the environment outside of the housing; and
    circuitry in the housing in communication with the first electrode, the second electrode, and the pressure sensor, the circuitry configured to determine, at a first time during a cardiac cycle, a first impedance between the first electrode and the second electrode and also a corresponding first pressure via the pressure sensor, resulting in a first impedance-pressure data pair.

2. The LCP of claim 1, wherein the circuitry is configured to wirelessly transmit the first impedance-pressure data pair to a remote device.

3. The LCP of claim 1, wherein the circuitry is configured to determine, at a second time during the cardiac cycle, a second impedance between the first electrode and the second electrode and also a second pressure via the pressure sensor, resulting in a second impedance-pressure data pair.

4. The LCP of claim 3, wherein the first time corresponds to an S1 heart sound and the second time corresponds to an S2 heart sound.

5. The LCP of claim 3, wherein the circuitry is further configured to determine, at a plurality of times between the first time and the second time, a plurality of corresponding impedances between the first electrode and the second electrode and also corresponding pressures via the pressure sensor, resulting in a plurality of additional impedance-pressure data pairs.

6. The LCP of claim 5, wherein the circuitry is further configured to wirelessly transmit the first impedance-pressure data pair, the second impedance-pressure data pair, and the plurality of additional impedance-pressure data pairs to a remote device.

7. The LCP of claim 6, wherein the remote device is configured to generate and display a pressure-volume loop that is based at least in part on the first impedance-pressure data pair, the second impedance-pressure data pair, and the plurality of additional impedance-pressure data pairs.

8. The LCP of claim 7, wherein the remote device is configured to store and display a plurality of pressure-volume loops generated over a period of time.

9. The LCP of claim 1, wherein the circuitry is further configured to record contextual data regarding a patient's metabolic demands.

10. The LCP of claim 1, wherein the circuitry is configured to determine, at a first time during each of a plurality of cardiac cycles, the first impedance between the first electrode and the second electrode and also the corresponding first pressure via the pressure sensor, resulting in the first impedance-pressure data pair for each of the plurality of cardiac cycles.

11. The LCP of claim 10, wherein the circuitry is further configured to average the first impedance and the first pressure over the plurality of cardiac cycles, resulting in an averaged first impedance-pressure data pair.

12. The LCP of claim 1, wherein the circuitry comprises:
    energy delivery circuitry operatively coupled to the first electrode and the second electrode for causing a current to flow between the first electrode and the second electrode;
    detection circuitry operatively coupled to the first electrode and the second electrode for detecting an electrical signal received between the first electrode and the second electrode.

13. The LCP of claim 12, wherein the energy delivery circuitry provides a current between the first electrode and the second electrode and the detection circuitry measures a resulting voltage between the first electrode and the second electrode to determine the impedance between the first electrode and the second electrode.

14. The LCP of claim 12, wherein the energy delivery circuitry provides a voltage between the first electrode and the second electrode and the detection circuitry measures a resulting current between the first electrode and the second electrode to determine the impedance between the first electrode and the second electrode.

15. The LCP of claim 12, wherein the energy delivery circuitry is further configured to deliver pacing pulses via the first electrode and the second electrode.

16. The LCP of claim 12, wherein the detection circuitry is further configured to detect cardiac signals received between the first electrode and the second electrode.

17. A leadless cardiac pacemaker (LCP) configured to sense cardiac activity and to pace a patient's heart, the LCP comprising:
    a housing;
    a first electrode secured relative to the housing and exposed to the environment outside of the housing;
    a second electrode secured relative to the housing and exposed to the environment outside of the housing, the second electrode is spaced from the first electrode;
    a pressure sensor secured relative to the housing and is coupled to the environment outside of the housing; and
    circuitry in the housing in communication with the first electrode, the second electrode, and the pressure sensor, the circuitry configured to determine, at each of a plurality of times during each of a plurality of cardiac cycles, an impedance between the first electrode and the second electrode and also a corresponding pressure via the pressure sensor, resulting in a plurality of impedance-pressure data pairs for each of the plurality of cardiac cycles.

18. The LCP of claim 17, wherein the circuitry is further configured to wirelessly transmit at least some of the plurality of impedance-pressure data pairs for each of the plurality of cardiac cycles to a remote device.

19. The LCP of claim 18, wherein the remote device is configured to generate and display a pressure-volume loop based on the plurality of impedance-pressure data pairs for at least one of the plurality of cardiac cycles.

20. A system comprising:
    a leadless cardiac pacemaker (LCP) configured to sense and pace a patient's heart, the LCP comprising:
        a housing;
        a first electrode positioned proximate a distal end of the housing;
        a second electrode positioned proximate a proximal end of the housing, wherein a current flowing between the first electrode and the second electrode is used to calculate impedance;
        a pressure sensor; and
        circuitry in communication with the first electrode, the second electrode, and the pressure sensor;
    an external support device comprising a processor and a display;
    wherein the circuitry of the LCP is configured to sample impedance between the first electrode and the second electrode and pressure at a plurality of times within each of a plurality of cardiac cycles, and to generate a plurality of impedance-pressure data pairs, the circuitry of the LCP further configured to transit the plurality of impedance-pressure data pairs to the external support device via conducted communication; and
    wherein the external support device is configured to generate and display a pressure-volume loop using at least some of the plurality of impedance-pressure data pairs.

* * * * *